(12) United States Patent
Cornen

(10) Patent No.: US 10,420,869 B2
(45) Date of Patent: Sep. 24, 2019

(54) LEFT VENTRICULAR CARDIAC ASSIST PUMP AND METHODS THEREFOR

(71) Applicant: SYSTOL DYNAMICS, Marseilles (FR)

(72) Inventor: Alain Cornen, Marseilles (FR)

(73) Assignee: SYSTOL DYNAMICS, Marseilles (FR)

( * ) Notice: Subject to any disclaimer, the term of this patent is extended or adjusted under 35 U.S.C. 154(b) by 0 days.

(21) Appl. No.: 14/783,260

(22) PCT Filed: Apr. 8, 2014

(86) PCT No.: PCT/CA2014/050358
§ 371 (c)(1),
(2) Date: Oct. 8, 2015

(87) PCT Pub. No.: WO2014/165993
PCT Pub. Date: Oct. 16, 2014

(65) Prior Publication Data
US 2016/0045652 A1    Feb. 18, 2016

(30) Foreign Application Priority Data

Apr. 8, 2013 (FR) .................................. 13 53147
Apr. 8, 2013 (FR) .................................. 13 53148
Apr. 8, 2013 (FR) .................................. 13 53149

(51) Int. Cl.
A61M 1/10    (2006.01)
A61M 1/12    (2006.01)

(52) U.S. Cl.
CPC .......... *A61M 1/122* (2014.02); *A61M 1/1008* (2014.02); *A61M 1/1015* (2014.02);
(Continued)

(58) Field of Classification Search
CPC ....... A61M 1/101; A61M 1/122; A61M 1/125
See application file for complete search history.

(56) References Cited

U.S. PATENT DOCUMENTS 5,211,546 A    5/1993    Isaacson et al.
5,824,070 A    10/1998   Jarvik
(Continued)

FOREIGN PATENT DOCUMENTS

CA    2 472 088    9/2003
GB    2 451 161    1/2009
(Continued)

OTHER PUBLICATIONS

European Search Report issued in European Patent Application No. 14782766.1 dated Dec. 1, 2016.
(Continued)

*Primary Examiner* — Michael J D Abreu
(74) *Attorney, Agent, or Firm* — BakerHostetler

(57) ABSTRACT

A left ventricular cardiac assist pump includes an inlet opening and a discharge opening aligned in an axial direction. The pump includes a casing spaced from a stator and impeller, with at least one connecting spacer connecting the casing and the stator. The impeller is configured to direct the blood towards the casing and the discharge opening, so that blood flows through the pump principally between the casing and the rotor-stator assembly.

18 Claims, 21 Drawing Sheets

(52) U.S. Cl.
CPC ........ *A61M 1/1031* (2014.02); *A61M 1/1036* (2014.02); *A61M 1/127* (2013.01); *A61M 1/101* (2013.01); *A61M 2205/0266* (2013.01)

(56) References Cited

U.S. PATENT DOCUMENTS

| | | |
|---|---|---|
| 5,980,448 A | 11/1999 | Heilman et al. |
| 6,244,835 B1 | 6/2001 | Antaki et al. |
| 6,247,892 B1 * | 6/2001 | Kazatchkov ............. F04D 3/00 415/68 |
| 8,177,703 B2 * | 5/2012 | Smith ................ A61M 1/1031 600/16 |
| 2003/0233143 A1 | 12/2003 | Gharib et al. |
| 2005/0107657 A1 * | 5/2005 | Carrier .................... F04D 1/04 600/16 |
| 2009/0118567 A1 | 5/2009 | Siess |
| 2012/0088954 A1 | 4/2012 | Foster |
| 2012/0134832 A1 | 5/2012 | Wu |
| 2012/0172655 A1 | 7/2012 | Campbell et al. |
| 2014/0296615 A1 * | 10/2014 | Franano .............. A61M 1/1086 600/17 |

FOREIGN PATENT DOCUMENTS

| | | |
|---|---|---|
| WO | 2007/105842 A1 | 9/2007 |
| WO | 2007/112033 A2 | 10/2007 |
| WO | 2012/094525 A2 | 7/2012 |
| WO | 2012/158543 A1 | 11/2012 |

OTHER PUBLICATIONS

International Search Report (ISR) (PCT Form PCT/ISA/210) dated Jul. 3, 2014, in PCT/CA2014/050358.

* cited by examiner

LEFT VENTRICULAR CARDIAC ASSIST PUMP AND METHODS THEREFOR

REFERENCE TO RELATED APPLICATIONS

This application is the U.S. national stage of International Application No. PCT/CA2014/050358, filed Apr. 8, 2014, which claims the priorities of French Application No. 1353147, filed Apr. 8, 2013, French Application No. 1353148, filed Apr. 8, 2013, and French Application No. 1353149, filed Apr. 8, 2013, the disclosures of which are all incorporated herein by reference in their entireties.

FIELD OF THE INVENTION

The invention generally relates to left ventricular cardiac assistance devices and methods.

BACKGROUND OF THE INVENTION

It is known that the human heart includes a right ventricle, which is used for circulation of venous blood (blue blood) and a left ventricle which serves for the circulation of arterial blood (red blood).

The blood from the venous system arrives into the right ventricle and leaves therefrom through the pulmonary artery which transports venous blood to the lungs.

Coming out of the lungs, oxygenated blood returns to the heart through the pulmonary veins, arrives into the left ventricle and leaves therefrom through the aorta towards the arterial system.

In the vast majority of cases, heart defects originate in the left ventricle.

It is known to use a pump to assist the heart in circulating blood in replacement of the left ventricle. This pump is typically part of a bypass arrangement implanted in parallel with the left ventricle.

Such a bypass system includes, in addition to the pump, an upstream end connected to a left ventricular tip and the other end connected to the inlet opening of the pump, and a downstream conduit having an extremity connected to a discharge opening of the pump and the other end connected to the aorta at the outlet of the left ventricle.

There are various known types of pumps that perform as left ventricular cardiac assist devices: in particular, centrifugal pumps with an inlet opening and a discharge opening that are arranged transversely to each other, and helical screw pumps with an inlet opening and a discharge opening aligned in an axial direction.

U.S. patent application U.S. 2012/0134832 describes a cardiac assist pump comprising an impeller rotor and a shaft provided with electric motor magnets and a casing having an intake opening and a discharge opening aligned in an axial direction. This casing includes a part forming a stator disposed around the rotor shaft, provided with stator windings of the electric motor, the magnets cooperating with the rotor shaft to rotate the latter.

Some pumps are designed to be implanted in a heart or in an artery. Such pumps are described for example in the U.S. patent application U.S. 2012/0088954 or UK Patent Application GB 2451161.

SUMMARY OF THE INVENTION

The present invention aims to provide a left ventricular cardiac assist pump, also referred to as a left ventricular assist device (LVAD), that offers good electrical and hydraulic performance.

The invention provides for this purpose a left ventricular cardiac assist pump, comprising an inlet opening and a discharge opening aligned along an axial direction, the pump comprising:
   a rotor comprising an impeller and a shaft provided with electric motor magnets, and
   a stator arranged around the shaft, provided with electric motor stator windings;
   characterized in that:
   the pump comprises a casing separate from the stator and radially spaced from said impeller and said stator, the rotor and the stator forming a rotor-stator assembly surrounded by the casing, with at least one connecting spacer connecting and offsetting the casing and the stator, said casing defining the inlet opening and the discharge opening of the pump, and
   the impeller is configured to circulate blood towards the casing and towards the discharge opening, whereby the blood flows into the pump principally between the casing and the rotor-stator assembly.

Because the casing is separate from the stator and surrounds the rotor-stator assembly, it is possible to provide a large cross-sectional passage between the casing and the rotor-stator assembly, and a very small gap between the rotor and the stator of the rotor-stator assembly.

This provides good blood circulation through the large area between the casing and the rotor-stator assembly and good electromagnetic cooperation between the stator and the rotor, through their proximity to each other.

In addition to the large passage area between the casing and the rotor-stator assembly providing improved blood circulation, the pump according to the invention is particularly well adapted to circulate blood therein since there is no sudden change of direction and the impeller, which is of the centrifugal type, with blood being driven towards the casing, does not disturb significantly the flow.

Therefore, the risks of haemolysis (breakdown of red blood cells) and thrombosis (clotting) are minimized.

In some implementations of the rotor-stator assembly:
   the rotor-stator assembly is generally spindle-shaped;
   the rotor comprises an upstream head connected to the shaft on the side of the inlet opening, said upstream head having an annular top, with an upstream face on the side of the inlet opening and a downstream face on the side of the shaft, the upstream and downstream faces extending from the annular top, said upstream face forming said impeller;
   the upstream face of the upstream head forming the impeller comprising blades projecting from a surface having a diameter decreasing from the annular top to the upstream extremity of the rotor;
   the downstream face of the upstream head has a surface with a diameter decreasing from the annular top to the shaft, the stator having on the side of the inlet opening an upstream surface inclined similarly to the surface of the downstream face of the upstream head, with upstream electromagnetic bearing magnets behind the surface of the downstream face of the upstream head and upstream electromagnetic bearing stator windings behind the upstream surface of the stator;
   the rotor comprises a downstream head connected to the shaft on the side of the discharge opening, said downstream head having an annular top, with an upstream face on the side of the shaft and a downstream face on the side of the discharge opening, the upstream and downstream faces extending from the annular top, the upstream face having a surface with a diameter decreasing from the annular top to the shaft, the stator having, on the side of the discharge opening, a downstream surface inclined similarly to the surface of the upstream face of the downstream head, with downstream electromagnetic bearing magnets behind the surface of the upstream face of the downstream head and downstream electromagnetic bearing stator windings behind the downstream surface of the stator;

the upstream face of the upstream head has a surface with a diameter decreasing from the annular top to the upstream extremity of the rotor, the casing having a diverging portion in relation to the upstream face of the upstream head, with electromagnetic bearing magnets behind the surface of the upstream face of the upstream head and electromagnetic bearing stator windings behind the internal surface of the diverging portion and/or the upstream face of the upstream head has a surface with a diameter decreasing from the annular top to the upstream extremity of the rotor, said pump having a support element supporting the upstream extremity of the rotor, said support element connected to the casing by arms.

In some implementations of the pump:

the casing is made of a solid structure having no apertures and substantial rigidity and each connecting spacer is made of a solid structure having no apertures and substantial rigidity;

the casing comprises a diverging portion, a straight portion and a converging portion, with the straight portion extending between the converging portion and the diverging portion, the diverging portion extending from an inlet extremity defining said inlet opening to said straight portion, and the converging portion extending from the straight portion to a discharge extremity defining said discharge opening, and/or the casing comprises eyelets on an external portion thereof for holding wires.

In other implementations of the pump:

the casing comprises a wall made of a shape memory resilient material and each connecting spacer comprises a wall made of a shape memory resilient material, and/or the rotor has a bore extending from an upstream extremity to a downstream extremity.

In other implementations of the pump:

an electrical cable runs along said connecting spacer, and/or each connecting spacer is helical and extends along said stator.

According to the present invention, there is also provided an assembly with a pumping unit, including a pump, a first connection fitting placed on the inlet extremity of the pump and a second connection fitting placed on the discharge extremity of the pump.

The first fitting and the second fitting are selected as corresponding to the diameter of the first portion of aorta (located between the coronary arteries and the intermediate portion) and the diameter of the second section of aorta (located between the intermediate portion and arterial brachiocephalic trunk).

To implant the pump, the intermediate portion of aorta is removed, the first fitting is secured to the first portion of aorta and the second fitting is secured to the second portion of aorta.

The assembly according to the invention allows one to implant a left ventricular cardiac assist pump in the place of a portion of the aorta between the coronary arteries and the brachiocephalic trunk.

The assembly pump according to the invention may thus be positioned in series with the left ventricle, unlike the conventional location mentioned-above which is parallel to the left ventricle, the pump being in a bypass comprising, in addition to the pump, an upstream conduit having an extremity connected to the left ventricular tip and a downstream conduit having an extremity connected to the aorta at the exit of the left ventricle.

The assembly pump according to the invention, when implanted, circulates blood in a closed circuit that is close to natural circulation.

The left ventricle can function well if it is able to do so. In this case, the combined flow generated by the left ventricle and the pump placed in series with the left ventricle allows for some pulsatility.

The left ventricle becomes unloaded while the bloodstream maintains close to a natural circulation, while filling of the right ventricle and kinetics of the right ventricle are facilitated.

The implantation of the pump is accomplished without affecting the left ventricle, such that it can continue to play a role in blood circulation, in particular by expanding to accommodate the volume of circulating blood, while complications linked to a connection on the left ventricular tip (left ventricular rhythm disorders, apical stasis likely to generate thromboembolic complications) are avoided.

The size of the implanted assembly being smaller than the size of conventional bypass system, the risk of infection is substantially decreased.

In the case where the left ventricle, after a certain period of assistance provided by the pump assembly, would recover so that the pump is no longer required, the lack of interference with the left ventricle allows removal of the pump and, in its place, a tubular prosthesis is sewn at one end on the first section of the aorta and at the other end on the second section of aorta.

The pump may be provided externally with eyelets for holding wires.

When the assembly pump is implanted, the holding wires pass through the eyelets and, for example, also pass through the sternum or eyelets attached to the sternum of the patient.

Thus, retention of the assembly pump is particularly efficient.

In other implementations of the system:

each connection fitting comprises a rigid connecting ring configured to be placed on said inlet extremity and said discharge extremity, and a flexible tube having one extremity secured to the rigid ring;

the flexible tubing is made of polyethylene terephthalate such as Dacron®;

the length of the pump is between 25 and 80 mm, preferably is above the aortic valve and above the coronaries with a length between 30 and 50 mm and most preferably between 30 to 40 mm; in any case, the length of the pump is selected to sustain proper blood flow in the patient through the aorta;

the outer diameter of the pump is between 15 and 60 mm, of higher diameter for anastomosis of the pump, and smaller diameters when the pump is to be inserted in the aorta.

each connection fitting is selected to correspond to the receiver's aorta diameter, the fitting preferably has a diameter of between 25 and 45 mm.

the pump comprises: a rotor comprising an impeller and a shaft provided with electric motor magnets; a stator disposed around said shaft, provided with electric motor stator windings, a casing separate of said stator, radially spaced from said stator and said impeller, the rotor and the stator forming a rotor stator assembly surrounded by the casing and at least one connecting spacer between the casing and the stator; said casing defining said inlet opening and said discharge opening of the pump; and the impeller is configured to flow the blood towards the casing and towards the discharge opening, whereby the blood flows into said pump principally between the casing and rotor-stator assembly, and/or said pump comprises a rotor having a bore from which projects a helical band, the rotor being provided with electric motor magnets, and a stator disposed around said rotor, provided with electric motor stator windings.

The invention also provides a method for providing a pumping unit for left ventricular cardiac assistance implantable on a predetermined patient, comprising the steps of:

providing a left ventricular cardiac assist pump having an inlet opening and a discharge opening aligned along an axial direction, said inlet opening being defined by an inlet extremity, said discharge opening being defined by a discharge extremity, said inlet and said discharge extremities being configured to each receive a connection fitting to a portion of an aorta, the length of said pump between the inlet extremity and the discharge extremity being less than the length of the portion of the aorta of said patient between coronary arteries and a brachiocephalic artery trunk, wherein said portion of the aorta comprises an intermediate section having a length similar to the length of the pump, a first section between the coronary arteries and the intermediate section, and a second section located between the intermediate section and the arterial brachiocephalic trunk;

determining the diameter of said first section of the aorta and the diameter of said second section of the aorta;

providing, according to the diameter determined for the first portion of the aorta, a first connection fitting configured to be placed on the inlet extremity of said pump and to be secured to the first section of the aorta;

providing, according to the diameter determined for the second section of the aorta, a second connection fitting configured to be placed on the discharge extremity of said pump and to be secured to the second section of the aorta and establishing a first connection on the inlet extremity and a second connection on the discharge extremity of the pump.

The invention also provides a method of implanting a left ventricular cardiac assist pump to on a predetermined patient, comprising the steps of:

implementing the method to provide a left ventricular cardiac assist pumping unit of as recited above;

removing said intermediate section of the aorta;

securing the first connection fitting to the first section of the aorta, and securing the second connection fitting to the second section of the aorta.

According to the present invention, there is also provided an assembly for implanting a left ventricular cardiac assist pump comprising an inlet opening and a discharge opening aligned in an axial direction, said pump having a stator and a rotor having an impeller, wherein:

said pump comprises a casing (separate from said stator), with the rotor and the stator forming a rotor-stator assembly surrounded by the casing, and at least one connecting spacer between the casing and the stator, the casing and connecting spacer being made of a resilient shape memory material and configured to, when subjected to a body temperature, in the absence of external constraints, assume a nominal configuration wherein the casing is radially spaced from the stator and the impeller, delimits said inlet opening and said discharge opening, and the casing, the connecting spacer and the rotor-stator assembly being configured such that, in the nominal configuration of the casing and the connecting spacer, the impeller in operation flows blood towards the casing and towards the discharge opening, wherein blood flows through said pump principally between the casing and the rotor-stator assembly and the casing and connecting spacer being configured to resiliently compress towards the rotor-stator unit under an effect of a radial compression, and said assembly further comprises a retention catheter in which said pump is arranged therein, in a configuration in which the casing and connecting spacer are collapsed on the rotor-stator assembly, said retention catheter having a smaller external diameter than an internal diameter of the casing in the nominal configuration.

The invention also provides a method for providing a pumping unit for implanting a left ventricular cardiac assist pump on a patient, comprising the steps of:

providing an assembly as described above;

installing in the patient a guide wire passing through an incision of the rib cage and an incision in the segment of the aorta between the coronary arteries and the brachiocephalic trunk, with the distal end of the guidewire disposed in the left ventricle;

sliding on the guide wire the assembly as described above until the assembly is in the aorta between the incision in the segment and the heart;

removing the retention catheter, and removing the guide wire.

DESCRIPTION OF DRAWINGS

These and other objects and advantages of the invention will become apparent upon reading the detailed description and upon referring to the drawings in which.

DETAILED DESCRIPTION

As will be further explained below, the LVAD described herein is configured to be implanted in parallel or preferably in series with the left ventricle, either in place of a removed portion of a patient's aorta between the heart and the first branches related to the arterial bloodstream or implanted within the aorta between the heart and the first branches of arterial bloodstream.

Figure 1:
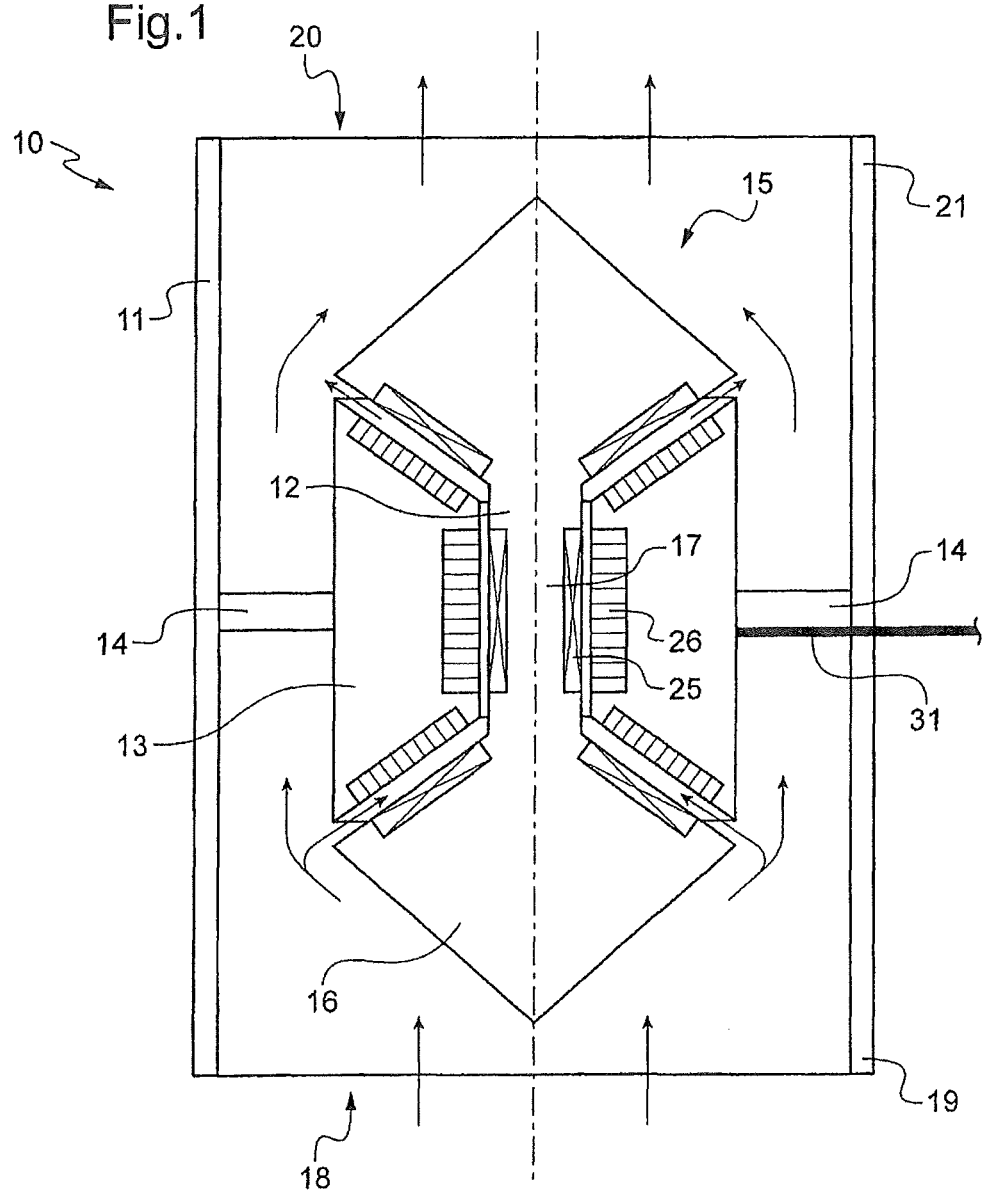
FIG. 1 is a cross-sectional view of a left ventricular cardiac assist pump according to an embodiment, wherein the rotor-stator assembly is shown in detail while the casing is shown schematically as well for the connecting spacers between the casing and the stator.

FIG. 1 presents the general configuration of the pump 10.

The pump 10 illustrated in FIG. 1 comprises a generally tubular casing 11, a rotor 12, a stator 13 and connecting spacers 14 between the casing 11 and the stator 13. In other figures, when the pump 10 is connected to connection fittings as described below, the pump 10 and connection fittings are generally designated as a pumping unit 50.

The rotor 12 and the stator 13 form a rotor-stator assembly 15, which is generally spindle-shaped.

The rotor 12 includes an impeller 16 and a shaft 17.

The stator 13 is positioned around the shaft 17, closer to the shaft 17 and close to the rotor 12.

The casing 11 is positioned around the rotor-stator assembly 15, being radially spaced from the stator 13 and impeller 16.

The casing 11 comprises an inlet opening 18 on a side which is seen at the bottom of FIG. 1. With the pump in operation, blood enters the pump 10 through the inlet opening 18.

The inlet opening 18 is delimited by an inlet extremity 19 of the casing 11.

On the side seen at the top of FIG. 1, the casing 11 has a discharge opening 20. With the pump in operation, blood leaves the pump 10 through the discharge opening 20.

The discharge opening 20 is defined by a discharge extremity 21 of the casing 11.

The inlet opening 18 and discharge opening 20 are aligned in an axial direction.

In general, the pump 10 is configured so that the blood flows between the inlet opening 18 and the discharge opening 20 substantially between the casing 11 and the rotor-stator assembly 15.

There is also a small flow of blood inside the rotor-stator assembly 15, between the rotor 12 and the stator 13.

In FIG. 1, the substantial blood flow between the casing 11 and the rotor-stator assembly 15 and the small flow of blood between the rotor 12 and stator 13 are shown by arrows.

The gap between the casing 11 and the rotor-stator assembly 15 is much larger than the gap between the rotor 12 and the stator 13.

This allows at the same time a good circulation of blood within the pump 10 through the large area between the casing 11 and the rotor-stator assembly 15, and good cooperation between the electromagnetic stator 13 and the rotor 12, through the close proximity between the stator 13 and the rotor 12.

The shaft 17 of the rotor 12 is provided with electric motor magnets 25. The stator 13 comprises, in proximity to magnets 25, electric motor windings 26. The magnets 25 and the windings 26 are used to rotate the rotor 12 in a well-known manner for electric motor technicians.

The fact that the rotor 12 includes simple magnets avoids the need to supply power to the rotor 12. Only the windings 26 of the stator 13 must be supplied with electricity.

The arrangement of the rotor 12 and the stator 13 will be described in detail later with reference to FIGS. 3 and 4.

The pump 10 is adapted to be secured through the housing 11 to the patient on which it is to be implanted.

Connecting spacers 14 rigidly secure the stator 13 to the casing 11. The connecting spacers 14 connect and offset the stator 13 and the casing 11. The shape of the connecting spacers 14 and the connection points between the connecting spacers 14 and the stator 13 can be at different locations along the stator 13 as shown, for example, in the different embodiments shown in FIG. 1 and in FIG. 19.

An electrical cable 31 runs along one of the connecting spacers 14 to supply power to the rotor-stator assembly 15, and more precisely to feed windings 26 and other stator 13 windings.

The electrical cable 31 is shown only in FIG. 1 to simplify the drawings.

Figure 2:
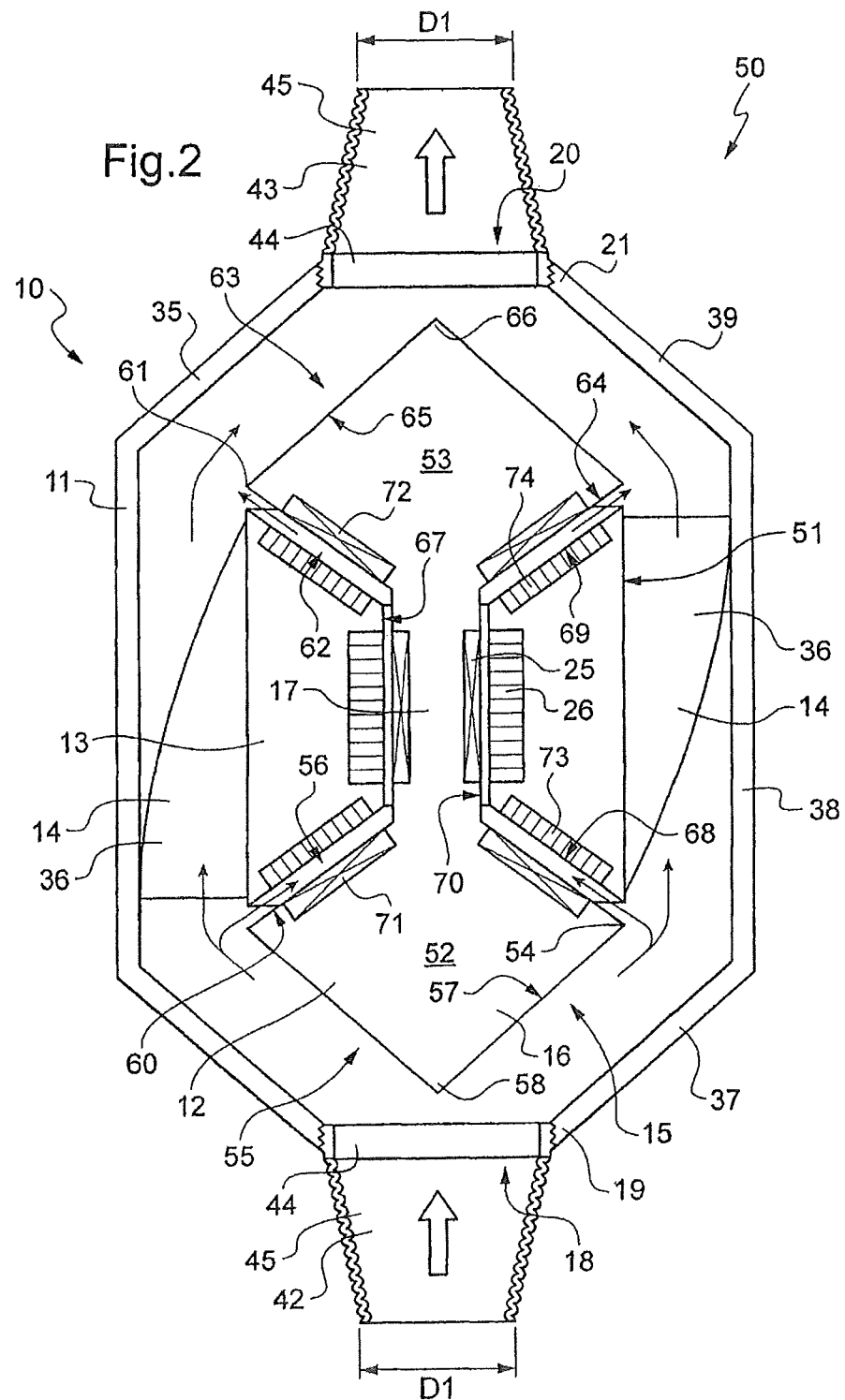
FIG. 2 is a view similar to FIG. 1 but showing in detail the casing and the connecting spacers according to a first embodiment of the pump and showing a fitting connected to a portion of the aorta on each extremity of the casing such that the pump and the fitting form a pumping unit.
Figure 3:
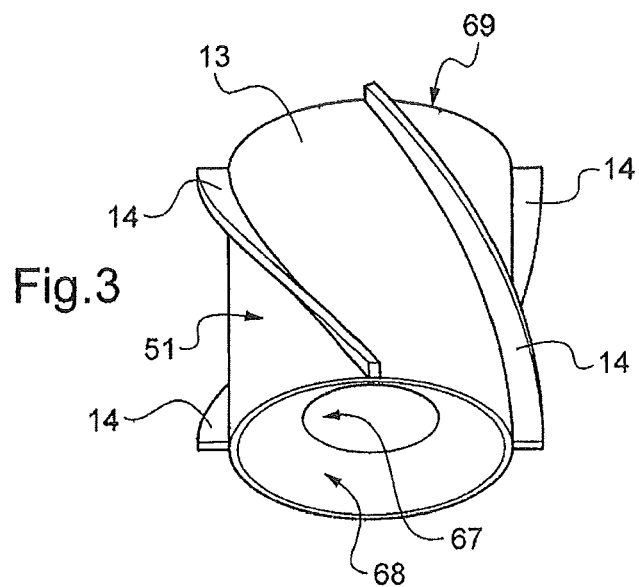
FIG. 3 is a perspective view of the stator and connecting spacers of the pump shown in FIG. 2.
Figure 4:
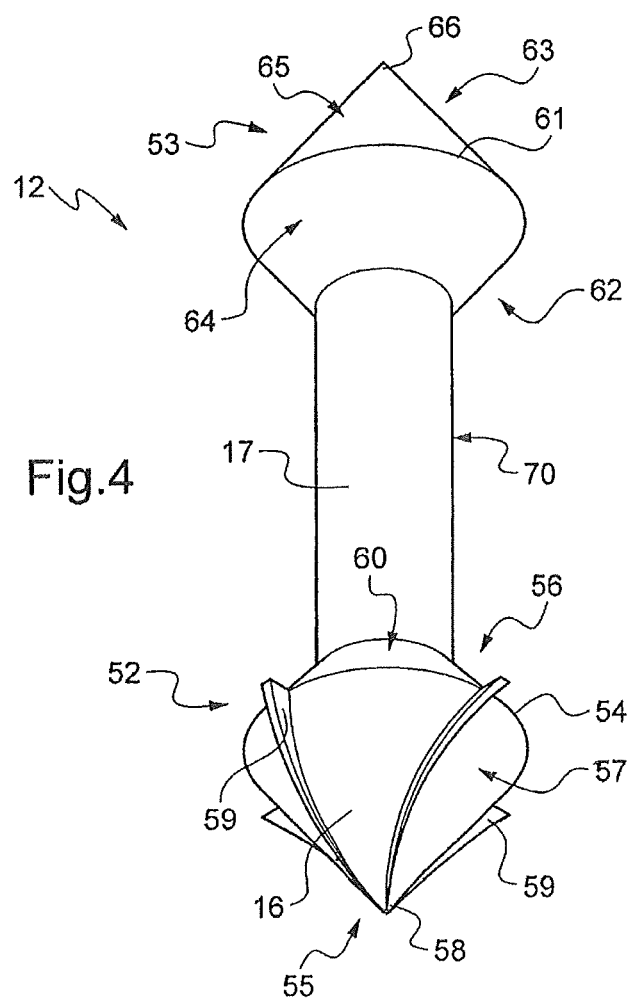
FIG. 4 is a perspective view of the rotor of the pump shown in FIG. 2.

Referring to FIGS. 2 to 4, a first embodiment of the pump 10 is disclosed. FIG. 2 shows the pumping unit to be serially connected (anastomosed) to the aorta. The casing 11 is a solid structure 35 having no apertures and substantial rigidity and the connecting spacers 14 are each made of a solid structure 36 also having no apertures and substantial rigidity.

In this first embodiment, the casing 11 comprises a diverging portion 37, a straight portion 38 and a converging portion 39.

The straight portion 38 extends between the diverging portion 37 and the converging portion 39. The diverging portion 37 extends from the inlet extremity 19 to the straight portion 38. The converging portion 39 extends from the straight portion 38 to the discharge extremity 21.

The rotor-stator assembly 15 is held by the connecting spacers 14 and centered with respect to the casing 11 both radially and axially.

The inlet opening 18 and discharge opening 20 have the same diameter.

The divergent portion 37, the straight portion 38 and the converging portion 39 are configured such that the radial gap between the casing 11 and the rotor-stator assembly 15 remains substantially constant. Thus, between the inlet opening 18 and the discharge opening 20, the area between the rotor-stator assembly 15 and the casing 11 remains substantially constant.

Figure 17:
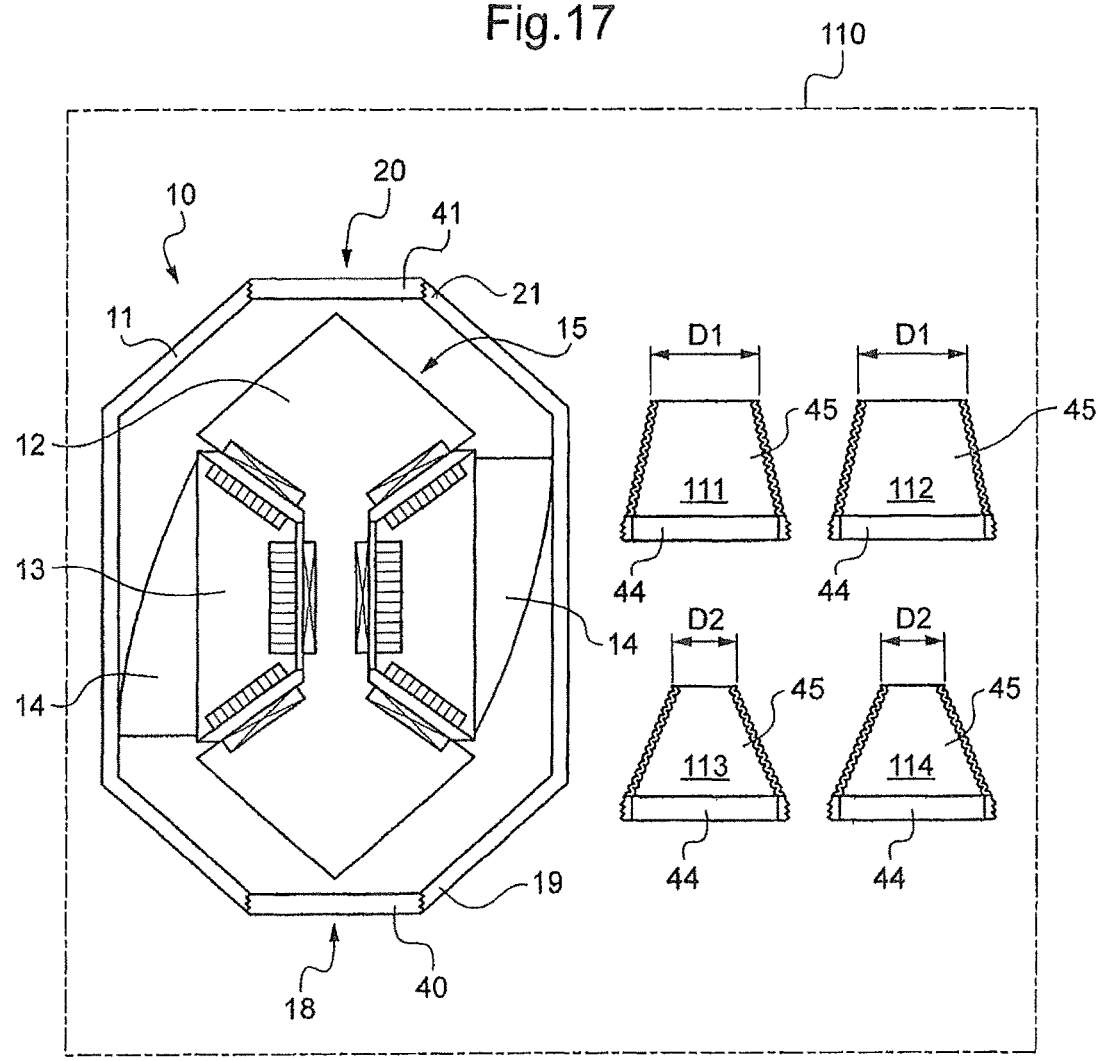
FIG. 17 is a schematic view of an assembly available to surgeons to implant the pump shown in FIGS. 2 and 16, this assembly comprising the pump and a set of four connection fittings, two of which having a first size and the other two having another size.

The inlet extremity 19 has an internal thread 40 (FIG. 17). The discharge extremity 21 has an internal thread 41 (FIG. 17).

The thread 40 is used for the implantation on the casing 11 of a connection fitting 42. The thread 41 is used for the implantation on the casing 11 of a connector fitting 43.

Each of the connection fittings 42 and 43 includes a rigid ring 44 and a threaded flexible tube 45 having one end secured to the ring 44. The flexible tubing 45 is of the type used to replace sections of artery. For example, the flexible tube 45 is made of a polyethylene terephthalate (PET) known as Dacron®.

The implantation of the connection fitting 42 on the casing 11 is done by screwing the ring 44 into the rigid thread 40 of the inlet extremity 19. Similarly, the implantation of the connection fitting 43 on the casing 11 is done by screwing the ring 44 into the rigid thread 41 to the discharge extremity 21.

When the pump 10 of FIG. 2 is thus equipped with connection fittings arranged respectively on the inlet extremity and the discharge extremity, a pumping unit implantable in a patient is provided.

As explained in greater detail below, the pumping unit 50 is configured to be implanted in place of a removed portion of a patient's aorta between the heart and the first branches related to the arterial bloodstream.

The distal end of the fitting 42 (opposite the end ring 44) is designed to be sewn to the aorta on the side of the heart. The distal end of the connector 43 is adapted to be sewn to the aorta on the arterial bloodstream side.

When the pumping unit 50 is implanted, the arterial blood leaving the heart, and more precisely the left ventricle of the heart, passes into the portion of the aorta upstream of the removed section, into the fitting 42, the pump 10, into the fitting 43 and the portion of the aorta downstream of the removed portion.

The direction of flow of blood through the fittings 42 and 43 is shown by an arrow in FIG. 2.

As seen in FIGS. 2 and 3, in the pump 10 of FIG. 2, there are four similar connecting spacers 14, with the same angular spacing between adjacent connecting spacers. Each connecting spacer 14 is in the form of a generally helical band which extends over the entire length of the outer cylindrical surface 51 of stator 13.

In addition to their function of providing a mechanical connection between the casing 11 and the stator 13, the connecting spacers 14 also perform a hydraulic function by linearizing the flow of blood passing through the space between the stator 13 and the casing 11.

In this space, as a result of being driven by the impeller 16 and circulating in a downstream flow direction, the blood tends to rotate around the stator 13.

The connecting spacers 14 counteract this effect and thus force the flow of blood to follow an axial direction.

The rotor 12 comprises a head 52 of the upstream side of the inlet extremity 19 (the side that can be seen at the bottom) and a downstream head 53 towards the discharge extremity 21 (the side that can be seen at the top).

The shaft 17 extends between the upstream and the downstream heads 52, 53.

The upstream head 52 has an annular top 54, from which respectively extend an upstream face 55 on the side of the inlet extremity 19 (the side that can be seen at the bottom) and a downstream face 56 on the side of the shaft 17 (the side which is seen at the top).

The upstream face 55 has a tapered surface 57 whose diameter decreases from the top 54 to the upstream extremity 58 of the rotor 12.

Blades 59 protrude from the surface 57, as shown only in FIG. 4 to simplify the drawings.

The upstream face 55 forms the impeller 16, which is configured to flow the blood towards the casing 11 and towards the discharge opening 23.

The downstream face 56 has a tapered surface 60 whose diameter decreases from the top 54 to the shaft 17.

The downstream head 53 has an annular top 61, from which respectively extend an upstream face 62 on the side of the shaft 17 (the side that can be seen at the bottom) and a downstream face 63 on the side of the discharge extremity 21 (side as seen at the top).

The upstream face 62 has a tapered surface 64 with a diameter decreasing from the top 61 to the shaft 17.

The downstream face 63 has a tapered surface 65 with a diameter that decreases from the top 61 to the downstream extremity 66 of the rotor 12.

The stator 13 has an inner surface 67 which is cylindrical, an upstream surface 68 disposed between the inner surface 67 and outer surface 51 towards the inlet extremity 19 (the side that can be seen on the bottom), and a downstream surface 69 disposed between the inner surface 67 and outer surface 51 towards the discharge extremity 21 (the side seen at the top).

The upstream surface 68 and the downstream surface 69 are concave. They are tapered with a decreasing diameter between the outer surface 51 and inner surface 67.

In general, the stator 13 is shaped to occupy the space around the shaft 17 between the downstream face 56 of the upstream head 52 and the upstream face 62 of the downstream head 53.

Thus, the diameter of the outer surface 51 of the stator 13 corresponds to the diameter of the top 54 of the upstream head 52 and the diameter of the top 61 of the downstream head 53, the length of the outer surface 51 corresponds to the distance between the tops 54 and 61, the diameter of the inner surface 67 of the stator 13 corresponds to the diameter of the outer surface 70 of the shaft 17, and the length of the inner surface 67 of the stator 13 corresponds to the length of the outer surface 70 of the shaft 17.

The spindle shape and the rotor-stator assembly promote favorable hydraulic performance of the pump 10.

The rotor 12 is provided, behind the surface 60 downstream face 56 of the upstream head 52, with upstream electromagnetic bearing magnets 71 and, behind the surface 64 of the upstream face 62 of the downstream head 53, with downstream electromagnetic bearing magnets 72.

The stator 13 includes behind the upstream surface 68, in proximity to bearing magnets 71, upstream electromagnetic bearing windings 73 and behind the downstream surface 69, in proximity to bearing magnets 72, downstream electromagnetic bearing windings 74.

The pairs of bearing magnets 71 and bearing windings 73 form, on the upstream side of the rotor-stator assembly 15, an electromagnetic bearing for centering the rotor 12 with respect to the stator 13 and take up axial forces exerted between the rotor 12 and the stator 13 in the upstream to downstream direction.

The pairs of bearing magnets 72 and bearing windings 74 form on the downstream side of the rotor-stator assembly 15, an electromagnetic bearing for centering the rotor 12 with respect to the stator 13 and take up the axial forces acting between the rotor 12 and the stator 13 in the downstream to upstream direction.

This capacity to simultaneously center the rotor and take up the axial forces is provided by the inclined orientation of the bearing magnets 71 and bearing windings 73 in the upstream and outward direction and by the inclined orientation of the bearing magnets 72 and bearing windings 74 in the downstream and outward direction. In some implementations, only one pair of bearing magnets and windings, either positioned upstream or downstream, can be used, such as the implementation shown in FIG. 5. In other implementations, both upstream and downstream pairs of bearing magnets and windings can be required as shown for example in FIG. 1, 2 or 19.

Figure 5:
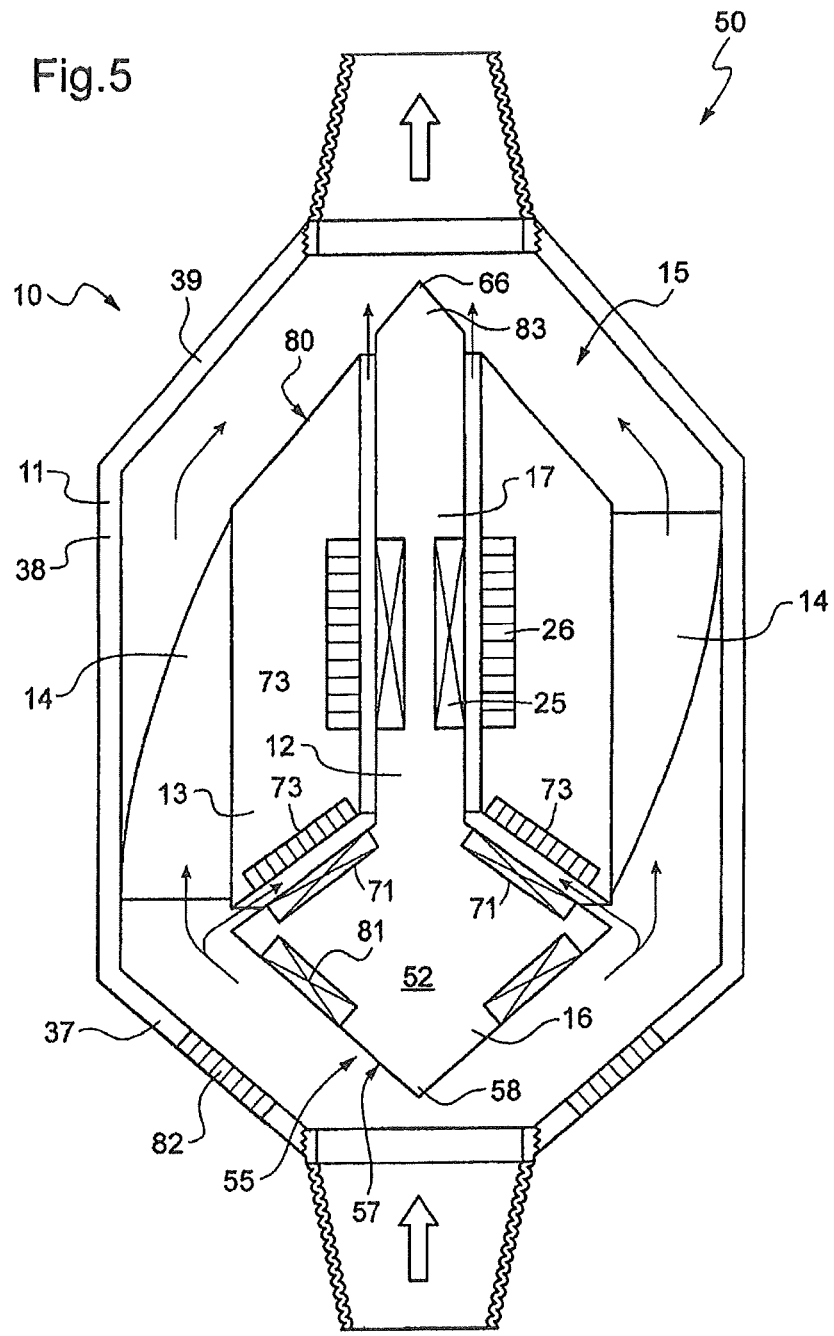
FIG. 5 is a view similar to FIG. 2 showing a variant of the rotational mounting of the rotor, further involving the casing.
Figure 6:
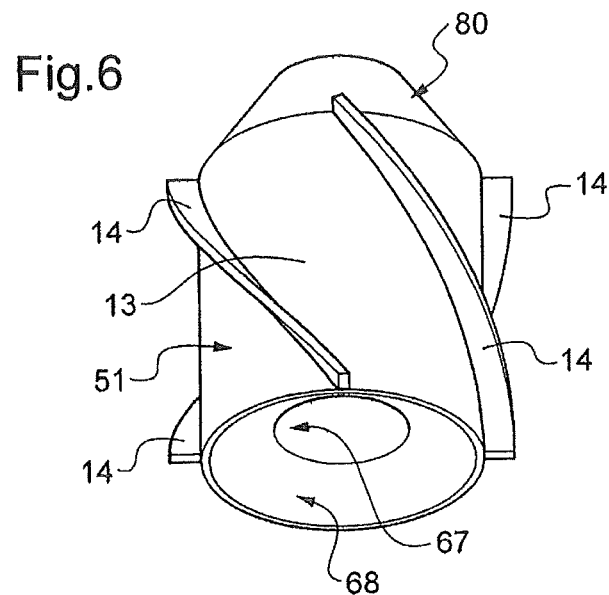
FIGS. 6 and 7 are views similar to those of FIGS. 3 and 4 but for the stator and the rotor of the pump shown in FIG. 5.
Figure 7:
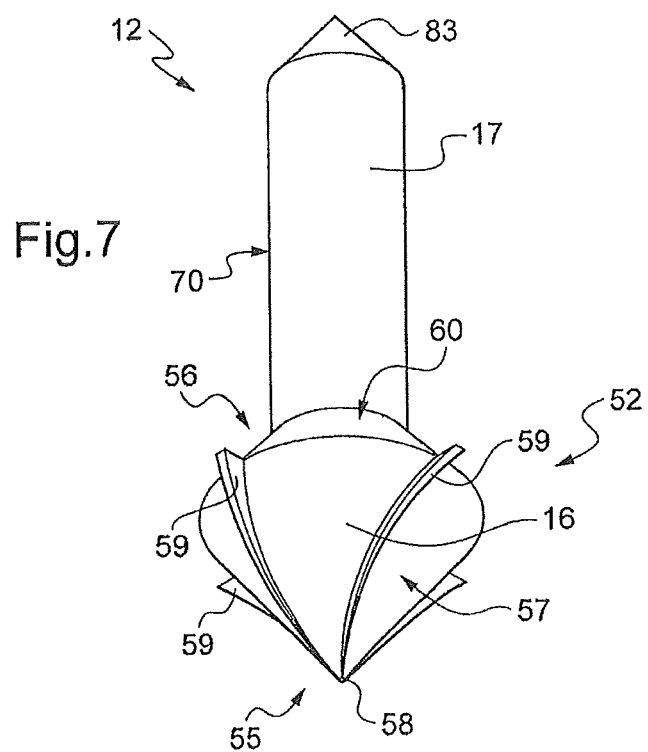

FIGS. 5-7 illustrate in the same way as FIGS. 2-4 a variant of the first embodiment of the pump according to the invention.

In this variant, the casing 11 comprises electromagnetic bearing windings with the rotor-stator assembly 15, while maintaining the general shape of the spindle, being arranged differently.

In this embodiment, the rotor 12 has no downstream head 53, the shaft 17 extending to the downstream extremity 66.

So that the rotor-stator assembly 15 retains a tapered shape, the downstream concave surface 69 of the stator 13 is replaced by a convex downstream surface 80. The surface 80 is frustoconical with a slope corresponding to the slope of the surface 65 of the downstream face 63 of the downstream head 53.

Similarly, the shaft 17 has a portion 83 projecting beyond the downstream surface 80. The portion 83 is tapered and is an extension of the downstream surface 80.

The downstream bearing magnets 72 are replaced by electromagnetic bearing magnets 81 located behind the surface 57 of the upstream face 55 of the upstream head 52. The downstream bearing windings 74 are replaced with electromagnetic bearing windings 82 located behind the internal surface of the divergent portion 37 of the casing 11. In some implementations, only one pair of electromagnetic bearing magnets and windings, either positioned upstream or downstream, can be used, such as the implementation shown in FIG. 5. In other implementations, both upstream and downstream pairs of electromagnetic bearing magnets and windings can be required.

Figure 8:
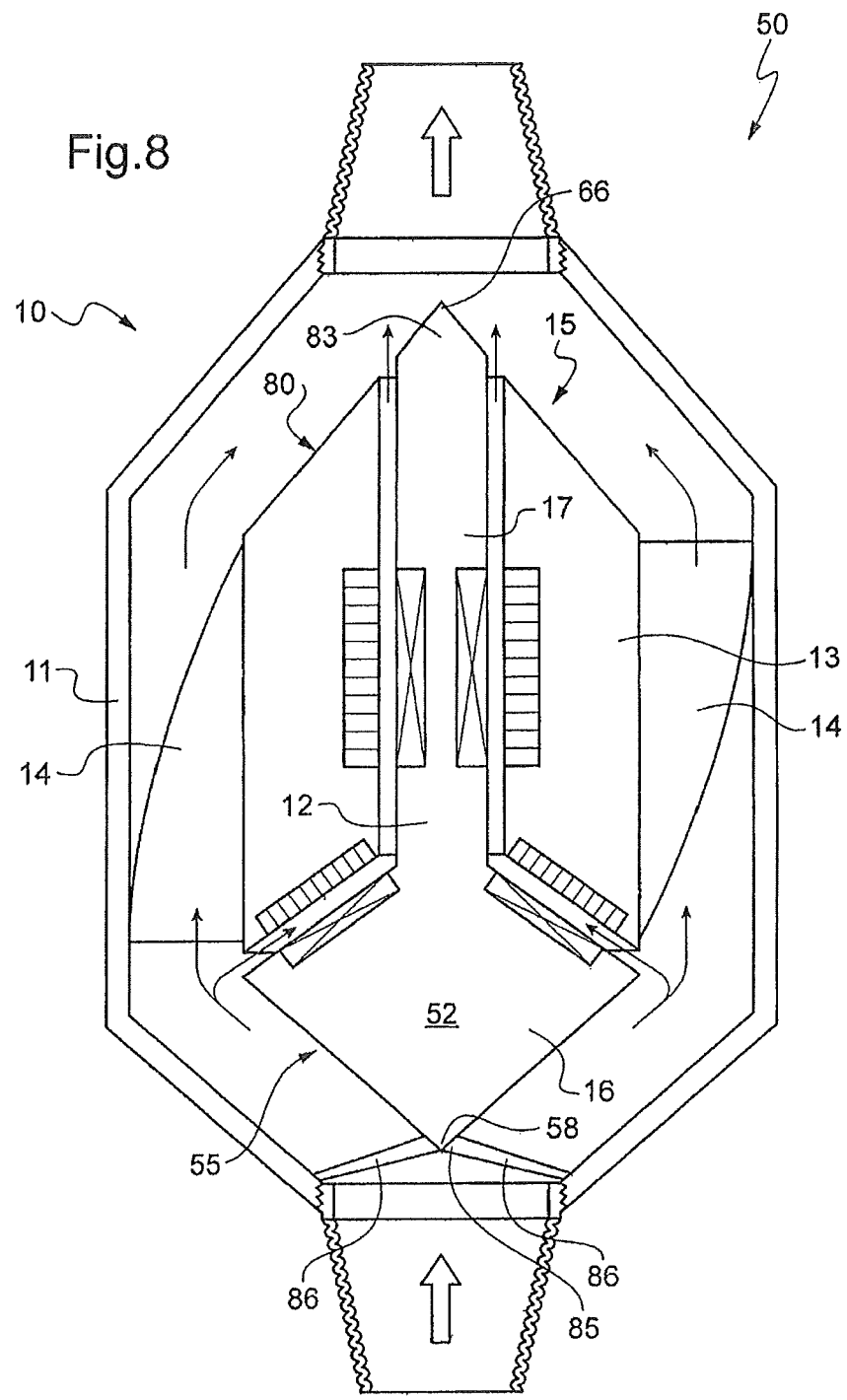
FIG. 8 is a view similar to FIG. 5, showing another embodiment of the rotational mounting of the rotor, including an abutment between the impeller and the casing.

FIG. 8 illustrates an embodiment similar to that of FIGS. 5-7, except that the electromagnetic bearing formed by the magnets 81 and the windings 82 is replaced by a mechanical bearing formed by the upstream extremity 58 of the rotor 12 and a support element 85 which supports the upstream extremity 58.

The support element 85 is connected to the casing 11 through arms 86.

Figure 9:
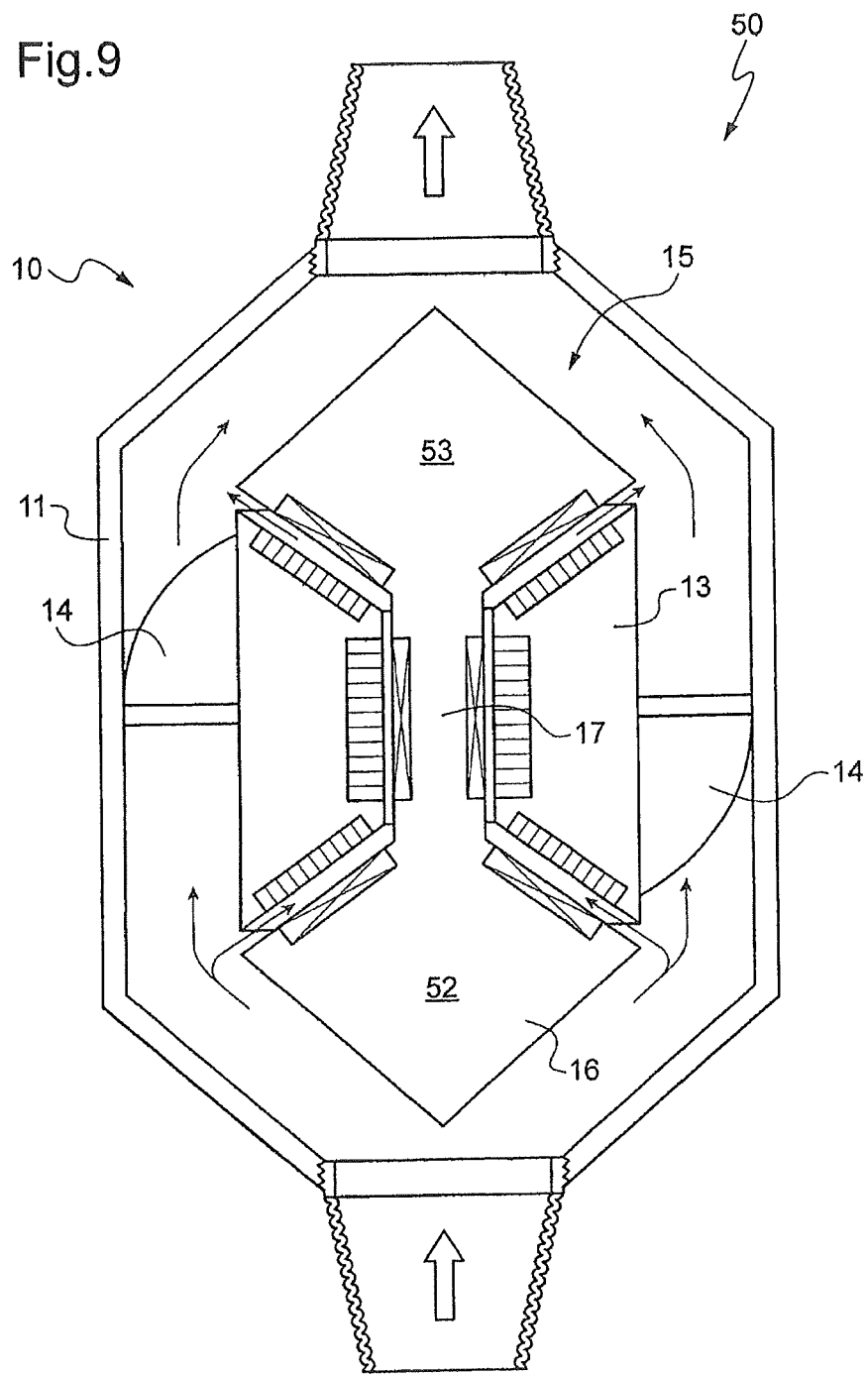
FIG. 9 is a view similar to FIG. 2 showing a variant of the connecting spacers.

FIG. 9 illustrates similarly as FIG. 2 another variant of the first embodiment of the pump according to the invention.

In this embodiment, the four connecting spacers 14 in the form of a helical band with ends offset by a quarter turn are replaced by two connecting spacers 14 in the form of a helical band with ends offset by a half turn.

Figure 10:
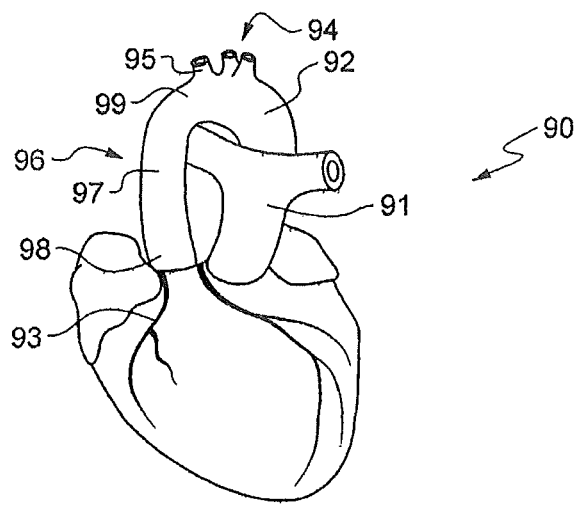
FIG. 10 is a perspective view of a patient's heart and arteries linked to the heart, namely coronary arteries, the aorta and the pulmonary artery.
Figure 11:
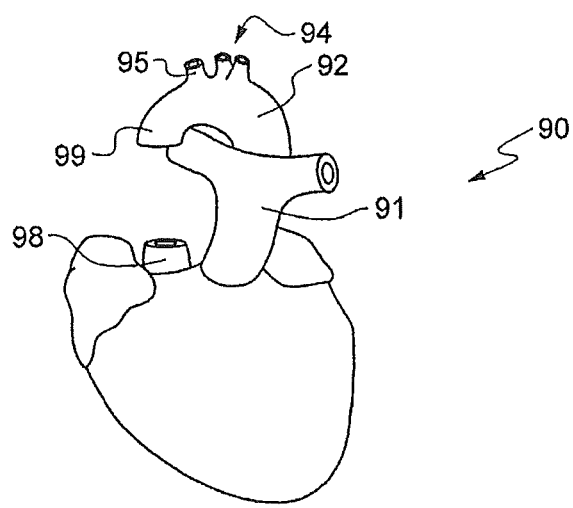
FIG. 11 is a view similar to FIG. 10 but with a section of the aorta that has been removed.
Figure 12:
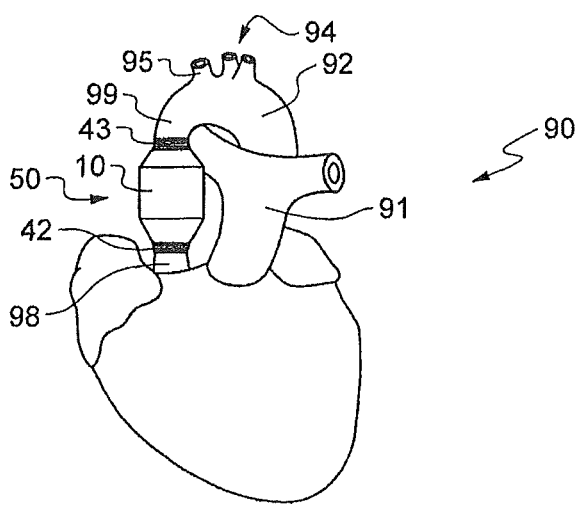
FIG. 12 is a view similar to FIG. 11 but with the pump according to the invention implanted in the location of the section of the aorta that has been removed.

FIGS. 10-12 show an implantation of a first embodiment of the pump 10, and, more precisely, the implantation of the pumping unit 50 including the first embodiment of the pump 10, the upstream connection fitting 42 put in place on the inlet extremity 19 and the downstream connection fitting 43 put in place on the discharge extremity 21.

FIG. 10 shows a human heart 90 and arteries connected the heart, namely the pulmonary artery 91, the aorta 92 and coronary artery 93.

The heart includes a right ventricle which serves for movement of venous blood (blue blood) and a left ventricle which serves for the circulation of arterial blood (red blood).

The blood from the venous bloodstream arrives into the right ventricle and leaves therefrom through the pulmonary artery 91 which takes the venous blood to the lungs.

Upon exiting the lungs, the oxygenated blood returns to the heart through the pulmonary veins, arrives into the left ventricle and leaves therefrom through the aorta 92 that leads to the arterial bloodstream.

Coronary arteries 93, which serve to irrigate the heart, are connected to the aorta 92 just as it leaves the heart 90.

To simplify the drawings, the coronary arteries 93 are shown only in FIG. 10.

At a certain distance of heart 90, the aorta includes the first branches of the arterial system, namely the supra-aortic trunks 94.

The trunk closest to the heart is the brachiocephalic trunk 95.

Between coronary arteries 93 and brachiocephalic trunk 95, the aorta 92 includes a segment 96 without any branching.

It is in the place of a portion of this segment, that a first embodiment of the pump 10, more precisely the pumping unit 50, is implanted.

To allow implantation on a predetermined patient, the length of the pump 10 to be implanted is less than the length of the segment 96.

The segment 96 of the aorta has an average diameter of 30 mm, and is generally between 25 and 45 mm. As known to a person of skill in the art, the diameter of the aorta can vary depending on the age and sex of the patient.

Preferably, the pump 10 has a length between 25 and 80 mm, preferably between 30 and 50 mm, preferably between 30 to 40 mm. In any case, the length of the pump is selected to sustain proper blood flow in the patient through the aorta.

Preferably, the flow rate of the pump 10 is between 1 to 8 L/min, preferably between 2 to 8 L/min with possible variations depending on the motor speed and thus can be higher). In any case, the flow must be sufficient to sustain proper blood flow in the patient through the aorta.

Because the LVAD described herein allows for the left ventricle to function well, if the left ventricle is able to do so, the flow generated by a capable left ventricle and the pump in series with the left ventricle allows for combined flow as well as some pulsatility.

The segment 96 comprises an intermediate section 97 having a length similar to the length of the pump 10, a first section 98 between the coronary arteries 93 and the intermediate section 97, and a second section 99 located between the intermediate section 97 and the brachiocephalic trunk 95.

To implant the pumping unit 50, the surgeon removes the intermediate section 97, as shown in FIG. 11.

Then, the surgeon secures the upstream connection fitting 42 to the first section 98 and secures the downstream connection fitting 43 to the second section 99.

To obtain the connection, the distal end of fitting 42 is sewn to the first section 98 and the distal end of fitting 43 is sewn to the second section 99.

FIG. 12 shows the pumping unit 50 once implanted.

Figure 13:
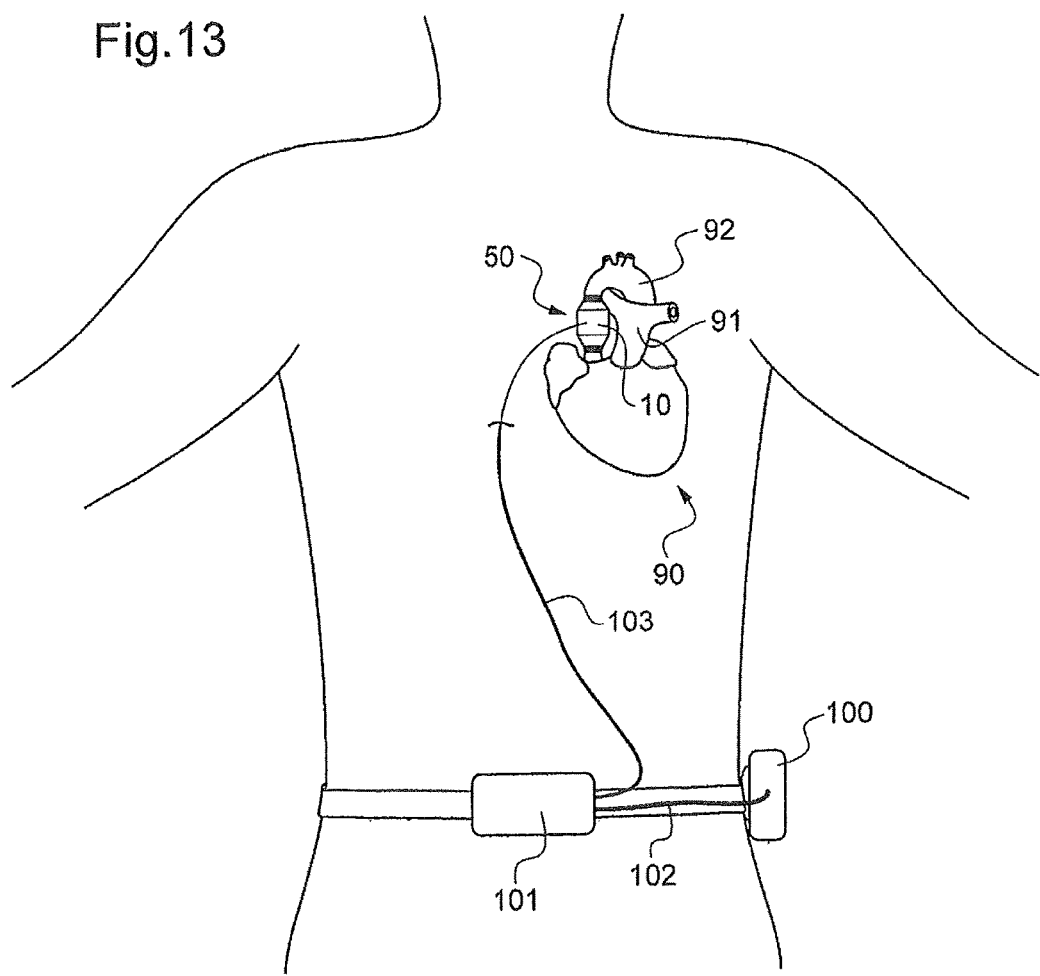
FIG. 13 is a schematic view of a patient showing the implanted pump and the electric supply cable for the pump and the patient's external equipment including a battery and an electronic control module of the pump.

For supplying power and for controlling the pump 10, as seen in FIG. 13, the patient is provided with an external device 100 having a battery and an electronic control module 101 connected to the battery 100 with a cable 102 and connected to the pump 10, with a cable 103.

Figure 14:
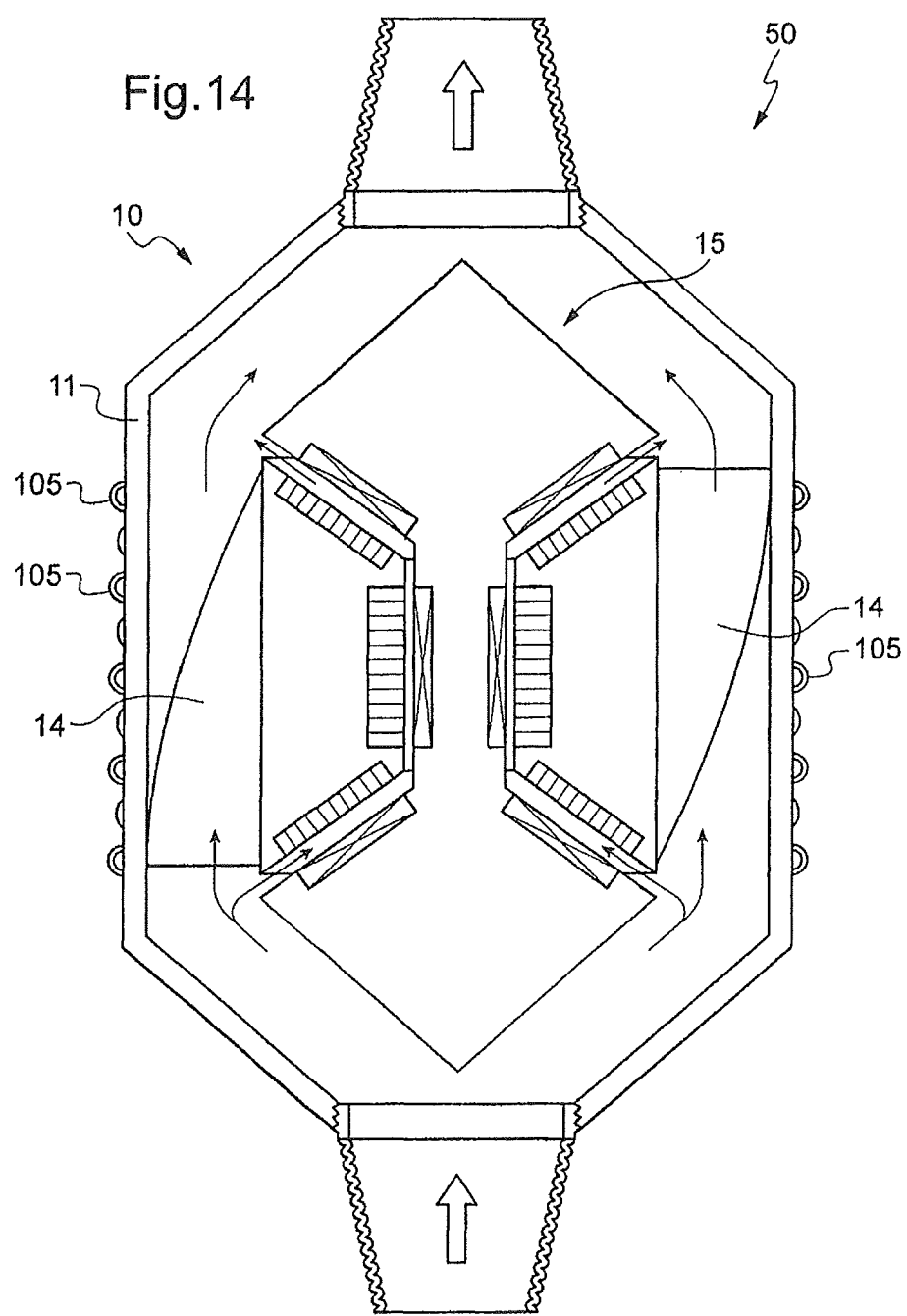
FIG. 14 is a view similar to FIG. 2 showing a variant of the casing, provided with eyelets on an external portion thereof for holding wires.

FIG. 14 illustrates in the same manner as FIG. 2 a variant of the first embodiment of the pump according to the invention, wherein the casing 11 is externally provided with eyelets 105 for holding wires.

Figure 15:
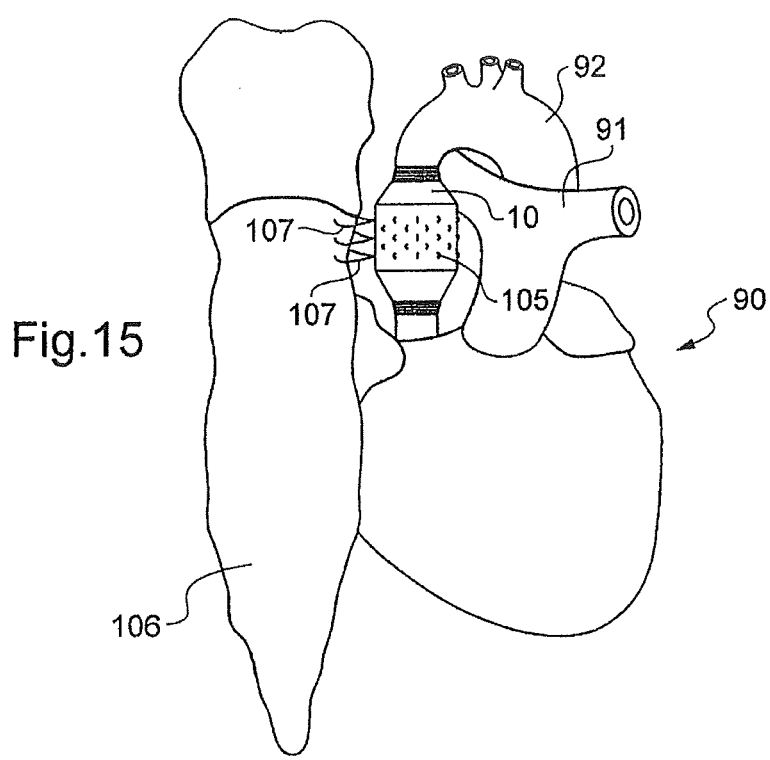
FIG. 15 is a view similar to FIG. 12 but for the pump shown in FIG. 14, also showing the patient's sternum and the holding wire linking the pump to the sternum.

FIG. 15 shows the same as FIG. 12 this embodiment of the pump once implanted and the patient's sternum 106 and the holding wires 107 implanted by the surgeon, passing through the eyelets 105 and through the sternum 106.

It is also possible to fix eyelets on the sternum 106 and to pass the holding wires 107 in the brackets attached to the sternum.

The holding wires 107 improve the attachment of the pumping unit 50 to the patient.

In variants not shown, the casing 11 of the pump 10 shown in FIGS. 5, 8 and 9 can also be provided with eyelets 105.

Figure 16:
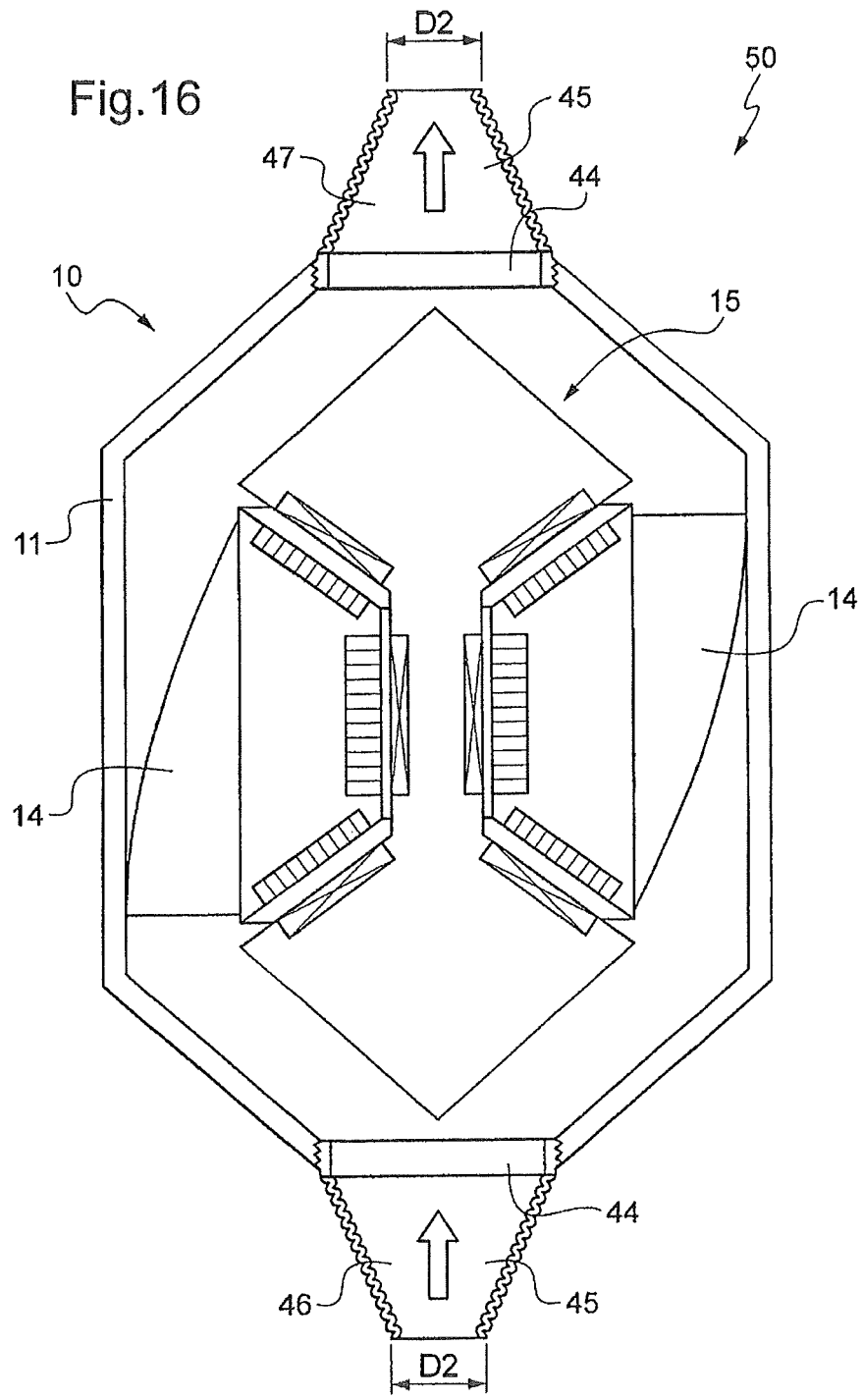
FIG. 16 is a view similar to FIG. 2 but with fittings of different size.

The pumping unit 50 shown in FIG. 16 is similar to the pumping unit 50 illustrated in FIG. 2, except that the upstream connection fitting 42 is replaced by a downstream connection fitting 46 and that the downstream connection fitting 43 is replaced by a downstream connection fitting 47.

The connecting fittings 46 and 47 are similar to connection fittings 42 and 43, except that the distal extremity of the fittings 42 and 43 have a diameter D1 and the distal extremity of the fittings 46 and 47 have a smaller diameter D2.

The pumping unit 50 illustrated in FIG. 16 is thus suitable for a patient having a smaller aorta.

FIG. 17 shows an assembly 110 for providing a pumping unit 50 implantable in a patient having a predetermined body size within a predefined range of body sizes.

The assembly 110 includes a pump 10 according to the first embodiment described above and four connection fittings 111, 112, 113 and 114.

The connection fittings 111 and 112 are designed as connection fittings 42 and 43. The connection fittings 113 and 114 are designed as connection fittings 46 and 47.

To prepare a suitable pumping unit 50 for a predetermined patient, the diameter of the first section 98 and the diameter of the second section 99 of the aorta are determined, for example through a scanner, and two fittings from fittings 111 to 114 are selected respectively depending on the diameter of the first section 98 to form the upstream connection fitting, and according to the diameter of the second section 99 to form downstream connection fitting.

In the example illustrated in FIG. 2, the fittings 111 and 112, both having a distal extremity diameter D1, were selected to form the upstream fitting 42 and downstream fitting 43 of the pumping unit 50.

In the example illustrated in FIG. 16, the fittings 113 and 114, both having a distal extremity diameter D2, have been selected to form the upstream fitting 46 and downstream fitting 47 of the pumping unit 50.

The patients in these examples share the same diameter for first section 98 and second section 99 of the segment 96 of the aorta 92.

In other patients, the diameter of the first section 98 and the diameter of the second section 99 are different.

In such a patient, one can take the connection fitting 113 of the upstream side and the connection fitting 111 of the downstream side to form the pumping unit 50.

The assembly 110 shown for example in FIG. 17, with four connection fittings of which two have the same diameter D1 and the two others a same smaller diameter D2, is suitable for a relatively narrow range of body sizes.

For a wider range of body types or for a finer adjustment to different body types, more connection fittings are provided with various dimensions of diameters.

In a non-illustrated variant, the attachment between the connection fittings such as 42, 43, 46, 47 and 111 through 116 with the embodiment of the pump 10 and/or 150 is carried out differently than by screwing components together. For example, a click-snap connection may be used.

Figure 18:
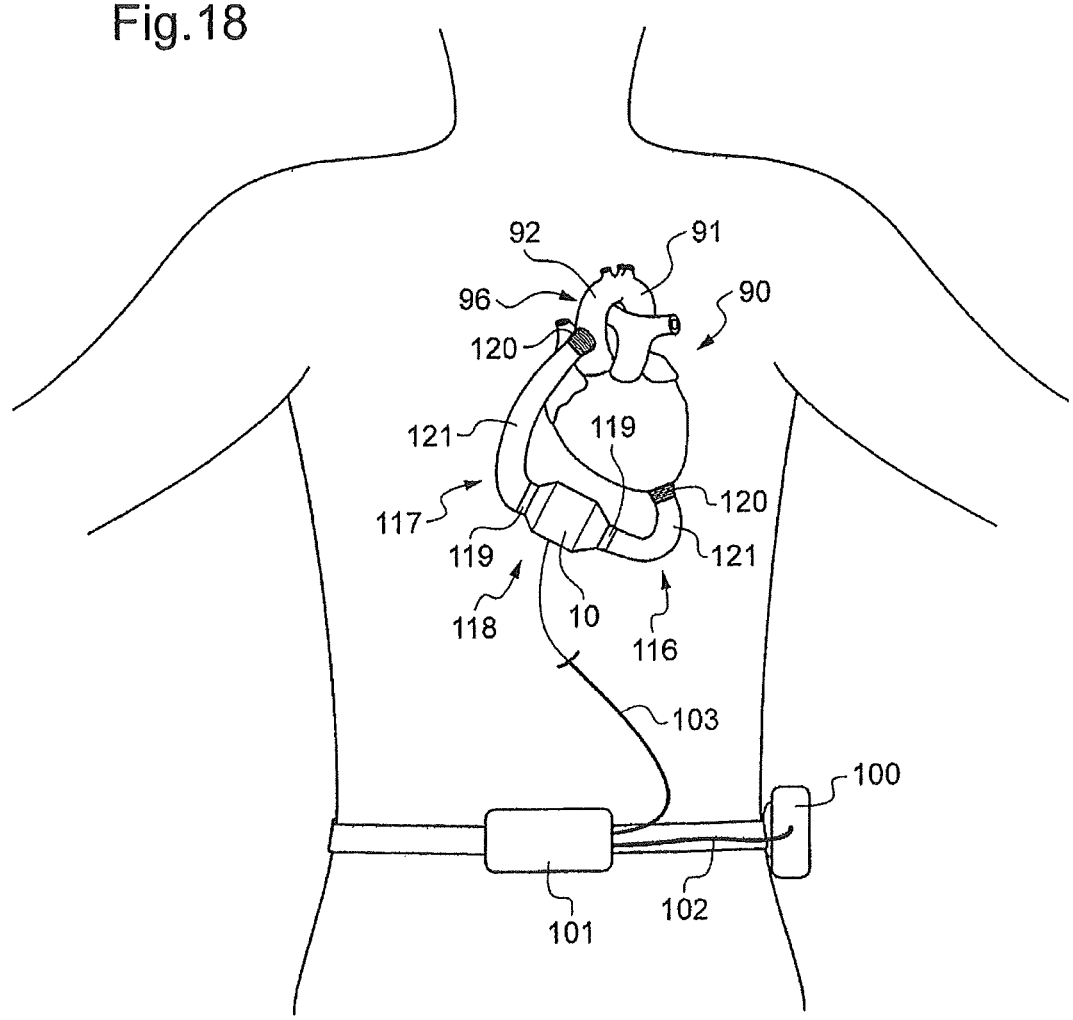
FIG. 18 is a view similar to FIG. 13 for an alternative implementation of the pump not positioned in series with the left ventricle replacing a section of the aorta, but rather in parallel to the left ventricle between the tip of the left ventricle and the aorta.

FIG. 18 illustrates similarly to FIG. 13 another way of implementing the first embodiment of the pump 10, namely in parallel with the left ventricle.

Rather than being provided with an upstream connection fitting such as connection fitting 42 or 46 and a downstream connection fitting such as connection fitting 43 or the connection fitting 47, the pump 10 according to the first embodiment is equipped with an upstream connection conduit 116 and a downstream connection conduit 117 to form a pumping unit 118.

The upstream connection conduit 116 and the downstream connection conduit 117 each have at one extremity a threaded rigid ring 119 similar to the rigid ring 44 of the connection fittings of the pumping unit 50. At the other extremity, the upstream connection conduit and downstream connection conduit include a tip 120 configured to provide a latero-terminal link.

Between the tip 120 and the rigid ring 119, the conduit 116 and the conduit 117 include a tube 121.

The ring 119 of the upstream connection conduit 116 is implanted by screwing into the inlet extremity 19 of the casing 11. The ring 119 of the downstream connection conduit 117 is implanted by screwing into the discharge extremity 21.

The tip 120 of the upstream connection conduit 116 is implanted by being sewn on the left ventricular tip of the heart 90, around an incision in the wall of the left ventricular tip.

The tip 120 of the downstream connection conduit 117 is implanted by being sewn to the segment 96 of aorta 92, around an incision in the wall of the aorta.

When the assembly 110 is implanted as shown in FIG. 18, it provides a bypass in parallel with the left ventricle. Blood is circulated through the bypass by the pump 10.

Figure 19:
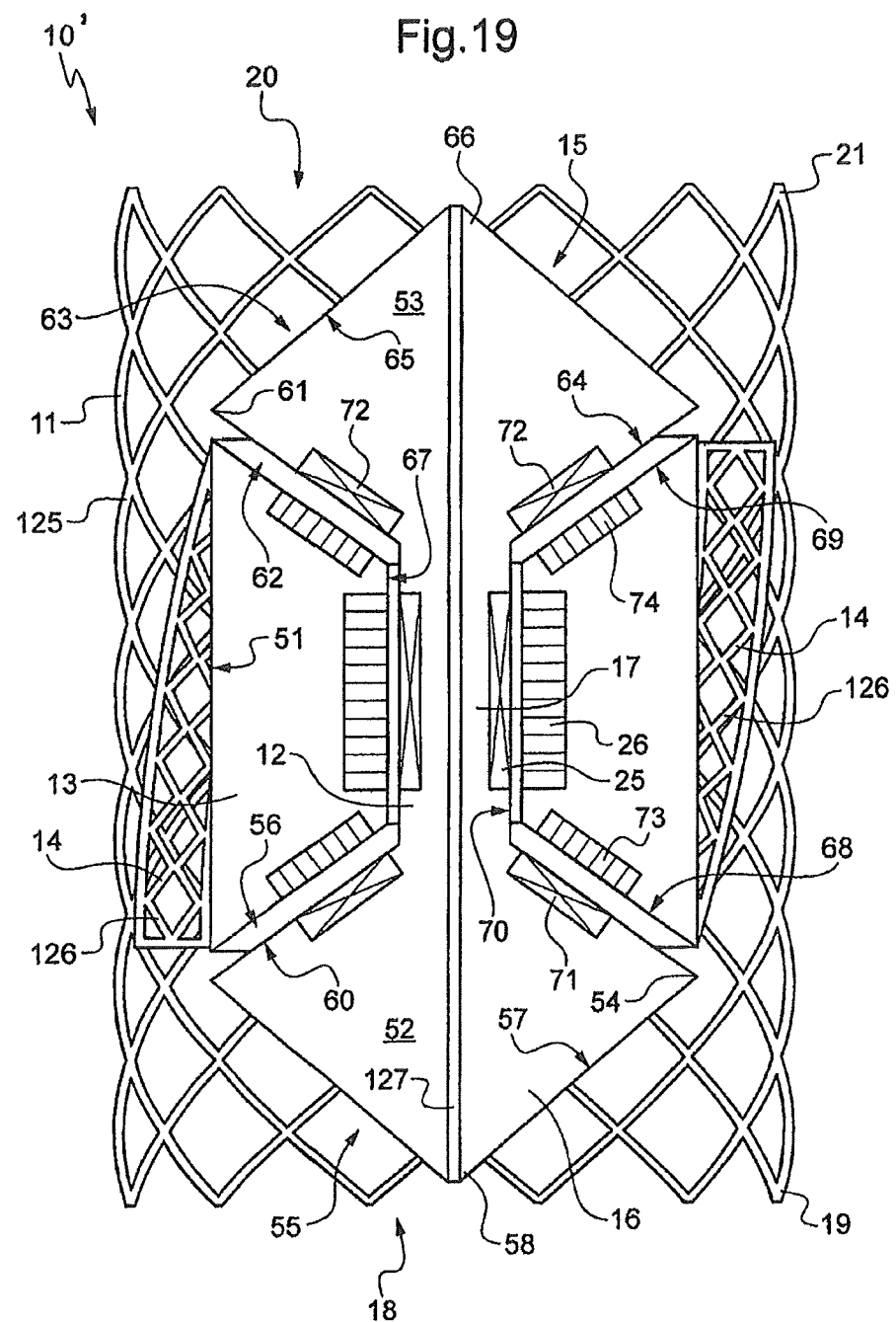
FIG. 19 is a view similar to FIG. 1 but showing in detail the casing and the connecting spacers of a second embodiment of the pump.
Figure 20:
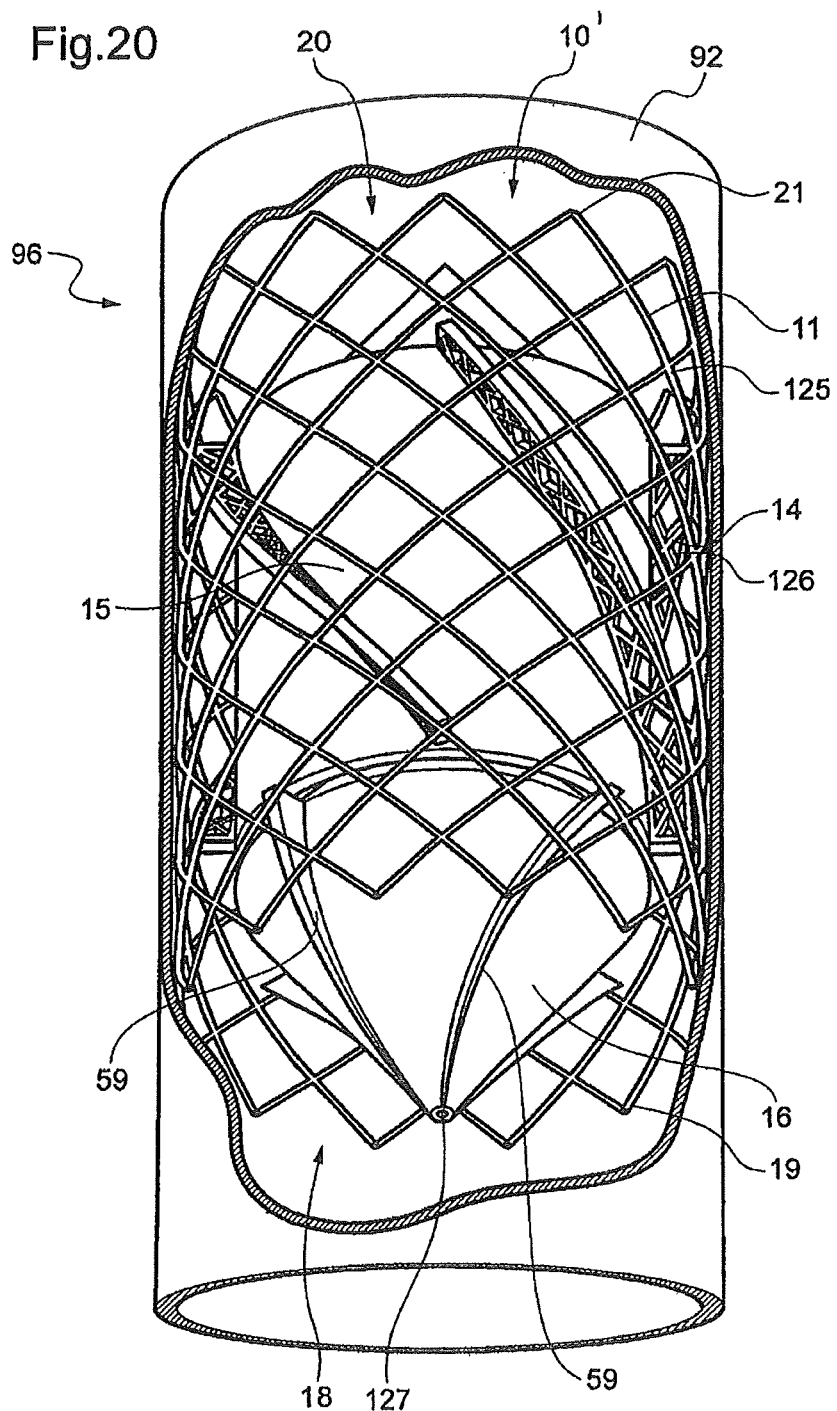
FIG. 20 is a perspective view of an aorta of a patient with the pump shown in FIG. 19 implanted therein, with a tear of the aorta wall to show the pump.

Referring to FIGS. 19 and 20, a second embodiment of the pump 10' is provided. This embodiment is for implanting the LVAD intra-aortically. The casing 11 is made of a mesh structure 125 made of a resilient shape memory material and wherein the connecting spacers 14 are each formed by a mesh structure 126 made of a resilient shape memory material. In other embodiments, the mesh structures can be replaced with any structure having an apertured or open configuration which facilitates the controlled transverse compression and then outward recovery of the pump during installation. The apertured configuration can comprise slits, slots or bigger openings. Such structures with an apertured configuration can be formed by cutting a tube. These structures can also be formed from criss-crossing wire and using an appropriate bonding technique at points where wires cross. The shapes of the apertures in the mesh structure will be selected to provide appropriate deformation characteristics, on both transverse compression prior to use and subsequently when the pump is installed. The shape of the apertures should also provide appropriate flexibility for the pump, prior to and during use.

The casing mesh structure 125 and connecting spacer mesh structures 126 are of the type used to make the arterial stents or percutaneous aortic valve casings.

Preferably, the casing mesh structure 125 and connecting spacer mesh structures 126 are made of an alloy of nickel and titanium known as Nitinol®.

The casing 11 formed by the mesh structure 125 and the connecting spacers 14 each formed by a mesh structure 126 are configured to assume, when subjected to body temperature, in the absence of external forces, the standard configuration of FIG. 1.

In the standard configuration of the second embodiment, the casing 11 is generally cylindrical.

The rotor-stator assembly 15 is held by the connecting spacers 14 and centered with respect to the housing 11 both radially and axially. Once again, the shape of the connecting spacers 14 and the connection points between the connecting spacers 14 and the stator 13 can be at different locations along the stator 13 as shown, for example, in the different embodiments shown in FIG. 1 and in FIG. 19.

As seen in FIG. 20, the pump 10' according to the second embodiment is intended to be implanted within the segment 96 of the aorta 92 located between the heart and the first branches of arterial bloodstream.

The inlet extremity 19 is adapted to be placed on the side of the heart of the patient. The discharge extremity 21 is adapted to be disposed on the side of the arterial bloodstream.

The casing 11 and the connecting spacers 14, thanks to the fact that the material of the mesh structure 125 and mesh structure 126 is a resilient shape memory material, are configured to compress resiliently towards the rotor-stator assembly 15 under the effect of radial compression.

The rotor 12 and the stator 13 have a substantial rigidity and therefore does not deform under the effect of a radial compression.

The rotor 12 is arranged like that of the pump 10 illustrated in FIGS. 2 and 3, except that the rotor 12 has a central bore 127 of smaller diameter extending from the upstream extremity 58 to downstream extremity 66.

The rotor-stator assembly 15 of the pump 10' of the second embodiment has preferably an external diameter smaller than the rotor-stator assembly 15 of the first embodiment.

In the standard configuration illustrated in FIG. 19, the casing 11 may have a larger diameter than the diameter of segment 96 of the aorta 92 in which the pump 10' is to be implanted.

Thanks to the elasticity of the material of the mesh structure 125 and mesh structures 126, the pump 10' is compressed when it is implanted in the aortic segment 96 and therefore exerts on it a radial force, which serves to immobilize the pump in the aorta.

The gap between the rotor-stator assembly 15 and the casing 11 and the wall of the aorta remains sufficient to allow good blood circulation.

The rotor-stator assembly has, for example, a diameter between 15 and 20 mm and the casing 11 has for example, in a standard configuration (excluding external stresses), an outer diameter between 30 and 60 mm, and smaller diameters when the pump is to be inserted in the aorta.

Figure 21:
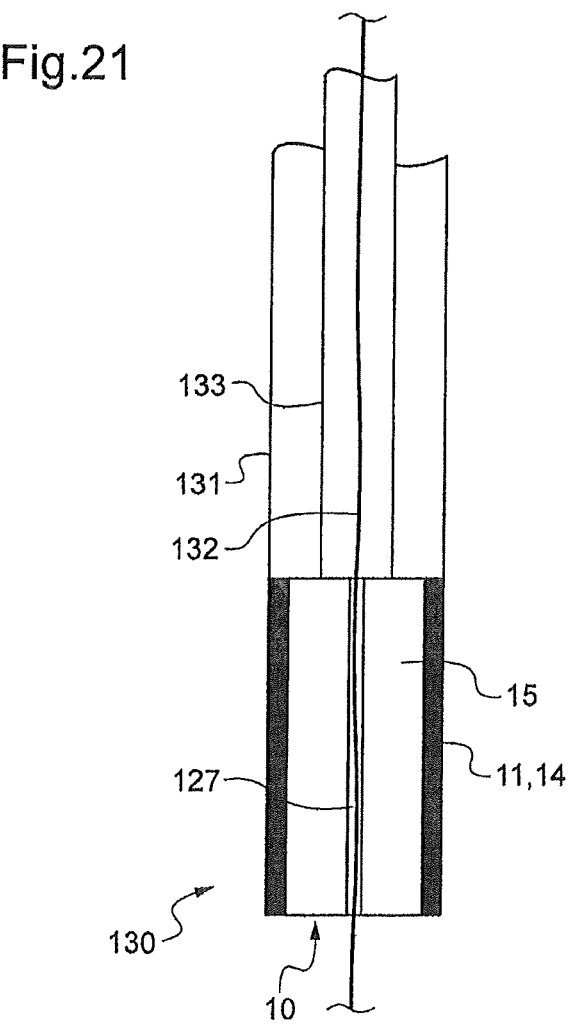
FIG. 21 is a schematic view of an assembly available to surgeons to implant the pump shown in FIGS. 19 and 20, including the pump and the elements enabling its placement in the aorta of a patient.

FIG. 21 shows an assembly 130 for implanting the pump 10' shown in FIGS. 19 and 20.

The assembly 130 includes a retention catheter 131 with a diameter smaller than the diameter of the casing 11 in the standard configuration and smaller that the diameter of segment 96 of the aorta in which the pump 10' is to be implanted.

The pump 10' is positioned in the enclosed retention catheter 131, in a configuration in which the casing 11 and the connecting spacers 14 are collapsed on the rotor-stator assembly 15.

In addition to the assembly 130 formed by the retention catheter 131 and the pump 10' contained in the catheter 131, a guidewire 132 and a transfer catheter 133 are used to implant the pump 10'. The transfer catheter 133 rests on one of the sides of the pump 10', in this case, the downstream side.

The guidewire passes through the transfer catheter 133 and into the central bore 127.

The assembly 130 and the transfer catheter 133 can slide along the guide wire 132.

To set up the pump 10', an incision 135 (FIG. 22) is carried out in the chest cavity of the patient as well as an incision 136 on the segment 96 of the aorta 92. Then, the guidewire 132 is inserted through the incision 135 and through the incision 136 until the distal extremity is placed in the left ventricle of heart 90, as shown in FIG. 22.

The part of guidewire 132 outside of the patient is passed through the bore 127 and in the transfer catheter 133. The transfer catheter 133 is pushed for passing the portion of the assembly 130 containing the pump 10 inside the segment 96 of the aorta 92.

Figure 22:
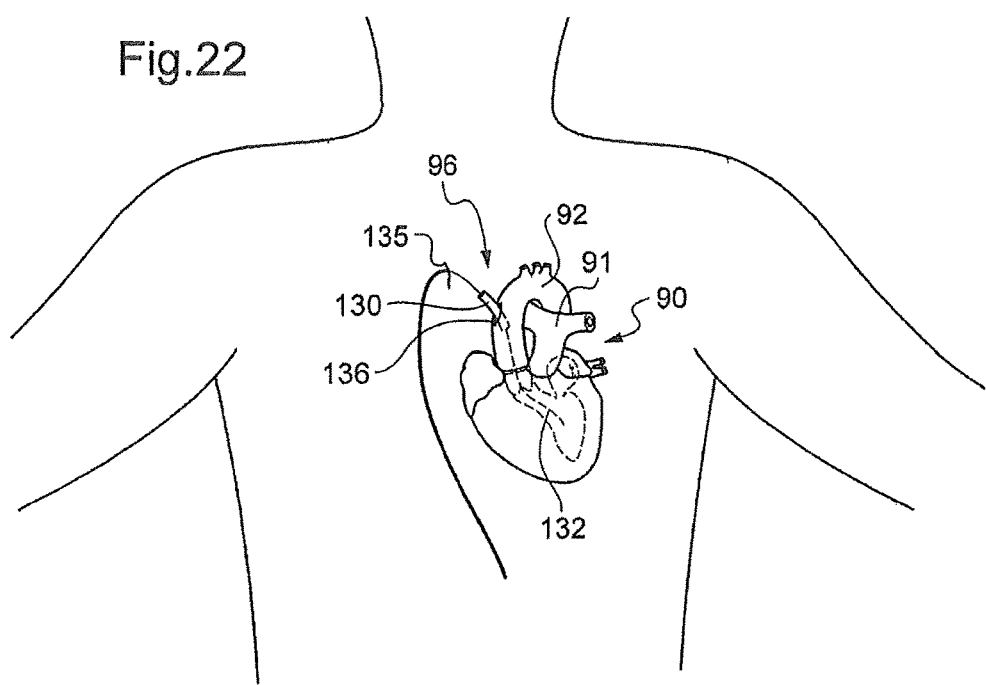
FIG. 22 is a perspective view of a patient showing the implantation of the pump in a portion of the aorta.

FIG. 22 shows the assembly 130 passing through the incision 136. To simplify the drawing, the transfer catheter 133 is not shown in FIG. 22 while only part of the retention catheter 131 is illustrated. In practice, the retention catheter 131 and the transfer catheter 133 protrude from the patient's body out of the incision 135.

Then the transfer catheter 133 is maintained firmly while pulling on the retention catheter 131 to extract the retention catheter 131.

During extraction of the retention catheter 131, the casing 11 and the connecting spacers 14 are deployed and come to bear against the wall of the aorta.

Once the retention catheter 131 has been removed, the transfer catheter 133 and the guidewire 132 are removed.

Figure 23:
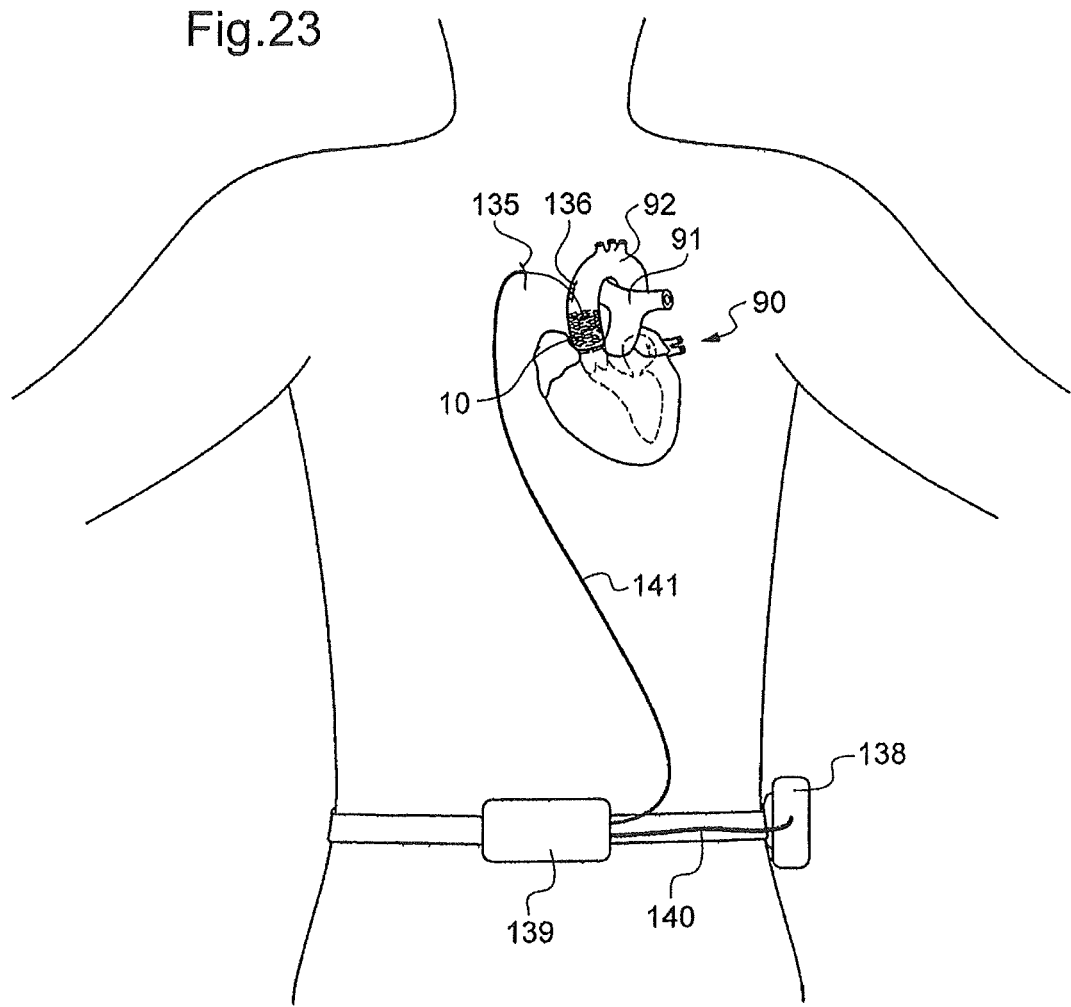
FIG. 23 is a schematic view of a patient showing the implanted pump, as well as the electric supply cable of the pump and the patient's external equipment having a battery and an electronic pump control module.

FIG. 23 shows the pump 10' once implanted.

For supplying power and for controlling the pump 10', the patient is provided with an external device 138 having a battery and an electronic control module 139 connected to the battery by a cable 140 and connected to the pump 10', preferably by a cable 141 positioned along with the pump 10.

In a non-illustrated variant, the mesh structure 125 of the casing 11 and the mesh structures 126 of the connecting spacers 14 are coated with a flexible coating closing the apertures. The flexible coating is for example a polyethylene terephthalate (PET) material known as Dacron®.

In non-illustrated variants, the pump 10 or pumping unit 50, are supplied and controlled by a capacitive coupling through the skin of the patient. More specifically, as known to a person of skill in the art, the pump or pumping unit is capable of communicating with a host controller or other external devices via a personal area network (PAN). A PAN transceiver can be used for communication with devices in contact with a user's body by propagating a current across the user's body via capacitive coupling. The wearable nature of the pump or pumping unit and the low power requirements of the PAN communication system enable the device to utilize alternative energy sources for powering the device.

The device may also include sensors for automatic adjustment of the pump to meet physiological demands of the patient.

In non-illustrated variants, pump 10, the surfaces facing the rotor 12 and stator 13, as opposed to being convex for the rotor 12 and concave for the stator 13, such as the surface 60 of the rotor 12 and the surface 68 of the stator 13, are inversely concave for the rotor 12 and convex for the stator 13.

In non-illustrated variants, the connecting spacers of the pump's are shaped differently, for example with the pump 10 shown in FIGS. 5 and 8 provided with the same connecting spacers as the pump as shown in FIG. 9, and/or the number of connecting spacers can be different, for example only one instead of four connecting spacers. In addition, although the optional configurations as illustrated in the accompanying drawings comprises various components and although the optional configurations of the connecting spacers as shown may consist of certain geometrical configurations as explained and illustrated herein, not all of these components and geometries are essential and thus should not be taken in their restrictive sense, i.e. should not be taken as to limit the scope of the present disclosure. It is to be understood that other suitable components and cooperations thereinbetween, as well as other suitable geometrical configurations may be used for the connecting spacers, and corresponding parts, as briefly explained and as can be easily inferred herefrom, without departing from the scope of the disclosure.

In non-illustrated variants, the impeller 16 is arranged differently, for example with fewer or more blades 59 or with blades being curved differently, the rotor 12 shaped differently and/or the rotor-stator assembly 15 shaped differently, by example with a form other than a spindle shape. In addition, although the optional configurations as illustrated in the accompanying drawings comprises various components and although the optional configurations of the impeller as shown may consist of certain geometrical configurations as explained and illustrated herein, not all of these components and geometries are essential and thus should not be taken in their restrictive sense, i.e. should not be taken as to limit the scope of the present disclosure. It is to be understood that other suitable components and cooperations thereinbetween, as well as other suitable geometrical configurations may be used for the impeller, and corresponding parts, as briefly explained and as can be easily inferred herefrom, without departing from the scope of the disclosure.

Figure 24:
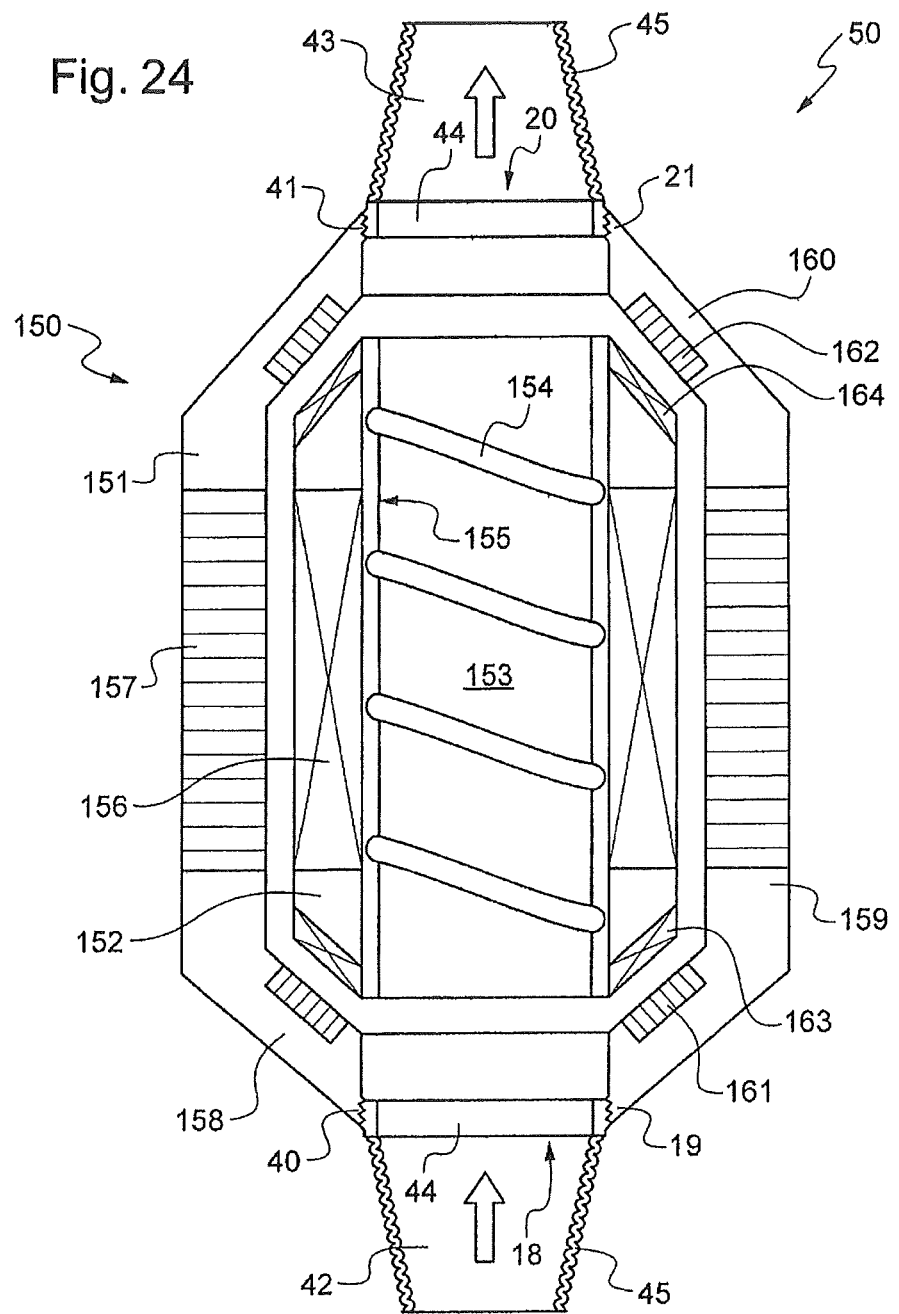
FIG. 24 is a view similar to FIG. 2 but for a variant of the pumping unit to be implanted at the location of the removed section of aorta.
Figure 25:
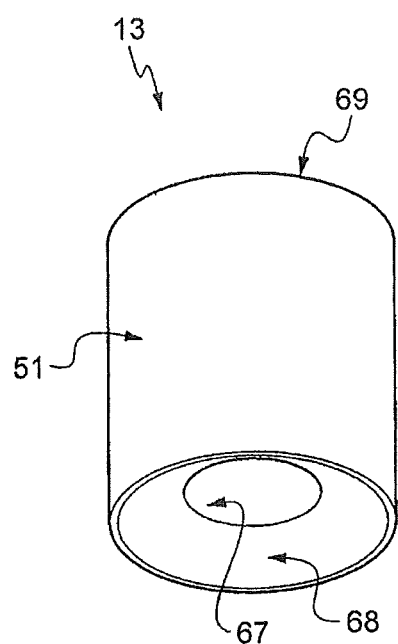
FIG. 25 is a perspective view of the basic structure of the stator, to show the general structure of the pump without connecting spacers.

Referring to FIG. 24, another implementation of the pumping unit 50 illustrated in FIG. 2 is shown.

In the embodiment shown in FIG. 24, the pump 10 is replaced by a pump 150 having a generally tubular casing 151 and a rotor 152.

The casing 151 is disposed around and adjacent the rotor 152.

Similar to the casing 11 of the pump 10, the casing 151 of the pump 150 has, on the side which is seen at the bottom in FIG. 24, an inlet opening 18. In operation, blood enters the pump 150 through the inlet opening 18.

The inlet opening 18 is delimited by an inlet extremity 19 of the casing 151.

On the side which is seen at the top in FIG. 24, the casing 151 has a discharge opening 20. In operation, blood leaves the pump 150 through the discharge opening 20.

The discharge opening 20 is defined by a discharge extremity 21 of the casing 151.

The inlet opening 18 and discharge opening 20 are aligned in the axial direction.

The rotor 152 has a relatively large diameter central bore 153. The diameter of the bore 153 corresponds to the diameter of the inlet opening 18 and discharge opening 20.

A helical band 154 projects into the bore 153 from the inner surface 155 of the rotor 152.

The pump 150 is configured so that the blood principally flows between the inlet opening 18 and discharge opening 20 in the bore 153, the blood being driven by rotation of the helical band 154.

There is also a small flow of blood between the rotor 152 and the casing 151.

The rotor 152 is provided with electric motor magnets 156. The casing 151 has, at the right of magnets 156, electric motor windings 157.

The magnets 156 and the windings 157 are used to rotate the rotor 152.

The casing 151 includes a diverging portion 158, a straight portion 159 and a converging portion 160.

The straight portion 159 extends between the diverging portion 158 and the converging portion 160. The diverging portion 158 extends from the inlet extremity 19 to the straight portion 159. The converging portion 160 extends from the straight portion 159 to the discharge extremity 21.

Similar to the pump 10 of the pumping unit 50 illustrated in FIG. 2, in the generally tubular casing 151 of the pump 150, the inlet extremity 19 has an internal thread 40 for the establishment of the connection fitting 42 while the discharge extremity 21 has an internal thread 41 for the establishment of the connection fitting 43.

In addition to the electric motor windings 157, which are located on the straight portion 159, the casing 151 has, on its divergent portion 158, the electromagnetic bearing windings 161, and on the converging portion 160 of the electromagnetic bearing windings 162.

In proximity to windings 161, the rotor 152 includes electromagnetic bearing magnets 163. In proximity to windings 162, the rotor 152 includes electromagnetic bearing magnets 164.

The magnets 163 and windings 161 form on the upstream side an electromagnetic bearing for centering the rotor 152 with respect to the casing 151, which forms the stator, and for compensating for the axial forces exerted between the rotor 152 and the generally tubular casing 151 in the downstream to upstream direction.

The magnets 163 and windings 161 form on the upstream side an electromagnetic bearing for centering the rotor 152 with respect to the casing 151, which forms the stator, and for compensating for the axial forces exerted between the rotor 152 and the generally tubular casing 151 in the downstream to upstream direction.

The capacity to simultaneously center the rotor and compensate for the axial forces is provided by the inclined orientation of the magnets 163 and windings 161 outwardly and towards the downstream direction and by the inclined orientation of the magnets 164 and windings 162 outwardly and towards the upstream direction.

The pumping unit 50 shown in FIG. 24 is used in exactly the same way as the other pumping units 50 described above.

Preferably, as known to persons skilled in the art, the components of the above-mentioned pumping unit are made of bio-compatible materials.

Although preferred embodiments of the present invention have been described in detail herein and illustrated in the accompanying drawings, it is to be understood that the invention is not limited to these precise embodiments and that various changes and modifications may be effected therein without departing from the scope of the disclosure.

The invention claimed is:

1. A left ventricular cardiac assist pump having an inlet opening and a discharge opening aligned along an axial direction of the pump, the pump comprising:
   a rotor comprising an impeller and a shaft provided with electric motor magnets;
   a stator arranged around the shaft and provided with electric motor stator windings; and
   a casing offset from the stator and radially spaced from the impeller and the stator thereby defining a radial gap therebetween, the rotor and the stator forming a rotor-stator assembly surrounded by the casing, with at least one connecting spacer connecting and offsetting the casing and the stator, the casing defining the inlet opening and the discharge opening of the pump,
   the impeller being positioned on a side of the inlet opening and configured to circulate blood within the radial gap, towards the casing and towards the discharge opening, the radial gap extending along the impeller and the stator so as to not obstruct the flow of blood and whereby the blood flows through the pump substantially within the radial gap between the casing and the impeller and stator.

2. The pump of claim 1, wherein the casing is made of a solid structure having substantial rigidity and each connecting spacer is made of a solid structure having substantial rigidity.

3. The pump of claim 2, wherein the casing comprises a diverging portion, a straight portion and a converging portion, with the straight portion extending between the converging portion and the diverging portion, the diverging portion extending from an inlet extremity defining the inlet opening to the straight portion, and the converging portion extending from the straight portion to a discharge extremity defining the discharge opening.

4. The pump of claim 3, wherein the impeller is positioned between the diverging portion and the straight portion of the casing.

5. The pump of claim 2, wherein the casing comprises eyelets on an external portion thereof for holding wires.

6. The pump of claim 1, wherein the rotor comprises an upstream head connected to the shaft, said upstream head having an annular top, with an upstream face on the side of the inlet opening and a downstream face on a side of the shaft, the upstream and downstream faces extending from the annular top, said upstream face forming said impeller.

7. The pump of claim 6, wherein the upstream face of the upstream head forming the impeller comprises blades projecting from a surface having a diameter decreasing from the annular top to an upstream extremity of the rotor.

8. The pump of claim 6, wherein the downstream face of the upstream head has a surface with a diameter decreasing from the annular top to the shaft, the stator having, on the side of the inlet opening, an upstream surface inclined similarly to the surface of the downstream face of the upstream head, with upstream electromagnetic bearing magnets being provided behind the surface of the downstream face of the upstream head and upstream electromagnetic bearing stator windings being provided behind the upstream surface of the stator.

9. The pump of claim 6, wherein the rotor comprises a downstream head connected to the shaft on the side of the discharge opening, said downstream head having an annular top with an upstream face on the side of the shaft and a downstream face on the side of the discharge opening, the upstream and downstream faces extending from the annular top, the upstream face having a surface with a diameter decreasing from the annular top to the shaft, the stator having on the side of the discharge opening a downstream surface inclined similarly to the surface of the upstream face of the downstream head, with downstream electromagnetic bearing magnets being provided behind the surface of the upstream face of the downstream head and downstream electromagnetic bearing stator windings being provided behind the downstream surface of the stator.

10. The pump of claim 6, wherein the upstream face of the upstream head has a surface with a diameter decreasing from the annular top to the upstream extremity of the rotor, the casing having a diverging portion in relation to the upstream face of the upstream head, with electromagnetic bearing magnets being provided behind the surface of the upstream face of the upstream head and electromagnetic bearing stator windings being provided behind an internal surface of the diverging portion of the casing.

11. The pump of claim 6, wherein the upstream face of the upstream head has a surface with a diameter decreasing from the annular top to the upstream extremity of the rotor, said pump comprising a support element supporting the upstream extremity of the rotor and being connected to the casing by arms.

12. The pump of claim 1, wherein the casing is made of a shape memory resilient material and the at least one connecting spacer is made of a shape memory resilient material.

13. The pump of claim 12, wherein the rotor has a bore extending from an upstream extremity to a downstream extremity.

14. The pump of claim 1, wherein the rotor-stator assembly is generally spindle-shaped.

15. The pump of claim 1, further comprising an electrical cable running along the connecting spacer.

16. The pump of claim 1, wherein the at least one connecting spacer is helical in shape and extends along the stator.

17. The pump of claim 1, wherein the length of the pump is between 25 mm and 80 mm and a diameter of the pump is between 15 mm and 60 mm.

18. The pump of claim 1, wherein the radial gap remains substantially constant throughout the pump.

\* \* \* \* \*